US010138462B2

(12) United States Patent
Klingemann

(10) Patent No.: US 10,138,462 B2
(45) Date of Patent: Nov. 27, 2018

(54) NATURAL KILLER CELL LINES AND METHODS OF USE

(75) Inventor: Hans Klingemann, Winnetka, IL (US)

(73) Assignee: NANTKWEST, INC., San Diego, CA (US)

( * ) Notice: Subject to any disclaimer, the term of this patent is extended or adjusted under 35 U.S.C. 154(b) by 2796 days.

(21) Appl. No.: 10/008,955

(22) Filed: Dec. 7, 2001

(65) Prior Publication Data
US 2002/0068044 A1 Jun. 6, 2002

Related U.S. Application Data

(63) Continuation-in-part of application No. 09/403,910, filed as application No. PCT/US98/08672 on Apr. 30, 1998, now abandoned.

(60) Provisional application No. 60/045,885, filed on Apr. 30, 1997.

(51) Int. Cl.
A61K 35/17 (2015.01)
C12N 5/00 (2006.01)
C07K 14/55 (2006.01)
C12N 5/0783 (2010.01)
A61K 35/12 (2015.01)

(52) U.S. Cl.
CPC ............ C12N 5/0093 (2013.01); C07K 14/55 (2013.01); C12N 5/0646 (2013.01); A61K 2035/124 (2013.01); C12N 2510/00 (2013.01)

(58) Field of Classification Search
None
See application file for complete search history.

(56) References Cited

U.S. PATENT DOCUMENTS 5,272,082 A 12/1993 Santoli et al.
5,772,995 A 6/1998 Fakhrai et al.
5,981,705 A 11/1999 Kornbluth

FOREIGN PATENT DOCUMENTS

WO WO 94/262841 11/1994

OTHER PUBLICATIONS

Tam et al., Human Gene Therapy, 10:1359-73, 1999.*
Gong Jiang-Hong, et al., "Characterization of a Human Cell Line (NK-92) with Phenotypical and Functional Characteristics of Activated Natural Killer Cells", *Leukemia*, vol. 8, No. 4 (Apr. 1994): pp. 652-658.
Klingemann, Hans-Georg, et al., "A cytotoxic ND-cell line (NK-92) for ex vivo purging of leukemia from blood", *Biology of Blood and Marrow Transplantation*, 2:68-75 (1996).
Wong, E., et al., Comparison of natural killer activity of human bone marrow and blood cells in cultures containing IL-2, IL-7 and IL-12, *Bone Marrow Transplantation*, (1996) 18, pp. 63-71.
Long, G. S., et al., "Lymphokine-Activated Killer Cell Purging of Leukemia Cells from Bone Marrow Prior to Syngeneic Transplantation", *Transplantation*, vol. 46, 433-438, No. 3, Sep. 1988.
Gambarcorti-Passerini, C., et al., "Selective purging by human interleukin-2 activated lyumphocytes of bone marrows contaminated with a lymphoma line or autologous leukaemic cells", *British Journal of Haematology*, 1991, 78, pp. 197-205.
Robertson, M. J., et al., "Biology and Clinical Relevance of Human Natural Killer Cells", *Blood*, vol. 76, No. 12, (Dec. 15, 1990): pp. 2421-2438.
Ellis, T. M., et al., "Functional Heterogeneity of Leu $19^{bright}$+ and Leu $19^{dim}$+ Lymphokine-Activated Killer Cells", *The Journal of Immunology*, vol. 142, Apr. 15, 1989, No. 8, pp. 2949-2954.
Ades, E. W., "Lymphokine-Activated Killer Cell Lysis of Human Neuroblatoma Cells: A Model for Purging Tumor Cells from Bone Marrow", *Clinical Immunology and Immunopathology*, 46, pp. 150-156 (1988).
Tsuchiyama, J. et al., "Characterization of a Novel Human Natural Killer-Cell Line (ND-YS) Established from Natural Killer Cell Lymphoma/Leukemia Associated with Epstein-Barr Virus Infection", *Blood*, vol. 92, No. 4, (Aug. 15, 1988): pp. 1374-1383.
Ingo, G. H., et al., "Use of a SCID Mouse/Human Lymphoma Model to Evaluate Cytokine-Induced Killer Cells with Potent Antitumor Cell Activity", *J. Exp. Med.*, vol. 174, Jul. 1991, pp. 139-149.
Hercend, T., et al., "Phenotypic and functional heterogeity of human cloned natural killer cell lines", *Nature*, vol. 301, Jan. 13, 1983, pp. 158-160.
Alderson, M. R., "Interleukin 7 Enhances Cytolytic T Lymphocyte Generation and Induces Lymphokine-activated Killer Cells from Human Peripheral Blood", *J. Exp. Med*, vol. 172, Aug. 1990, pp. 577-787.
Robertson, M. J., et al., "Response of Human Natural Killer (NK) Cells to NK Cell Stimulatory Factor (NKSF): Cytolytic Activity and Proliferation of NK Cells are Differentially Regulated by NKSF", *J. Exp. Med.*, Mar. 1992, pp. 779-788.
Phillips, J. H., et al., "Dissection of the Lymphokine-Activated Killer Phenomenon", *J. Exp. Med.*, vol. 164, Sep. 1986, pp. 814-825.

(Continued)

*Primary Examiner* — Michael Szperka
(74) *Attorney, Agent, or Firm* — Kilpatrick Townsend & Stockton LLP

(57) ABSTRACT

This invention relates to a natural killer cell line termed NK-92 and to NK-92 cell lines that have been modified by transfection with a vector to confer advantageous properties. Additionally, the invention provides an NK-92 cell, an NK-92 cell modified by transfection with a vector conferring advantageous properties, which is unable to proliferate and which preserves the effective cytotoxic activity. The invention provides a modified NK-92 cell line that is transfected with a vector encoding a cytokine that promotes the growth of NK-92 cells. In a significant embodiment, the cytokine is interleukin 2. The invention additionally provides a modified NK-92 cell line that is transfected with a vector that expresses a thymidine kinase gene. The invention further provides a modified NK-92 cell line that is transfected with a vector that expresses a $\beta_2$ microglobulin that has lost the ability to bind to T-cell receptors.

1 Claim, 16 Drawing Sheets
Specification includes a Sequence Listing.

(56) References Cited

OTHER PUBLICATIONS

Rosenberg, S. A., et al., "Special Report—Observation on the Systemic Administration of Autologous Lymphokine-Activated Killer Cells and Recombinant Interleukin-2 to Patients with Metastic Cancer", *The New England Journal of Medicine*, vol. 313, No. 23, Dec. 5, 1985, pp. 1485-1492.
Yodoi, J., et al., "TCGF (IL 2)-Receptor Inducing Factor(s)", *Journal of Immunology*, vol. 134, No. 3, Mar. 1985, pp. 1623-1630.
Mule, J. J., et al., "Adoptive Immunotherapy of Established Pulmonary Metastes with LAK Cells and Recombinant Interleukin-2", *Science*, vol. 225, pp. 1487-1489.
Komiyama, A., et al., "Childhood Lymphoblastic Leukemia with Natural Killer Activity: Establishment of the Leukemia Cell Lines Retaining the Activity", *Blood*, vol. 60, No. 6 (Dec. 1992), pp. 1429-1436.
Fernandez, L. A, et al., "Aggressive Natural Killer Cell Leukemia in an Adult With Establishment of an NK Cell Line", *Blood*, vol. 67, No. 4 (Apr. 1986): pp. 925-930.
Suzuki, N., et al., "Natural Killer Lines and Clones with Apparent Antigen Specificity", *J. Exp. Med.*, vol. 172, Aug. 1990. pp. 457-462.
Chin, Keh-Chuang, et al., "Activation and Transdominant Suppression of MHC Class II and HLA-DMB Promoters by a Series of C-Terminal Class II Transactivator Deletion Mutants", *The Journal of Immunology*, 0022-1767, 1997, pp. 2790-2794.
Schouten, Govert J., et al., "Downregulation of MHC Class I expression due to interference with p105-NFκB1 processing by Ad12E1A", *The EMBO Journal*, vol. 14, No. 7, pp. 1498-1507, 1995.

\* cited by examiner

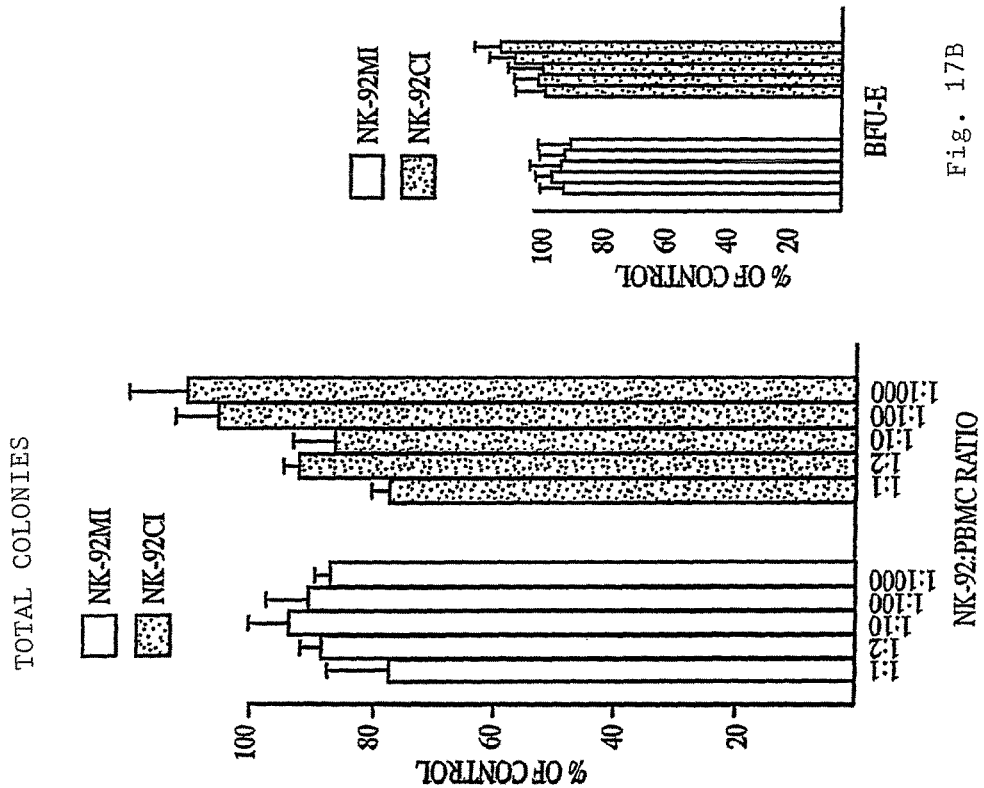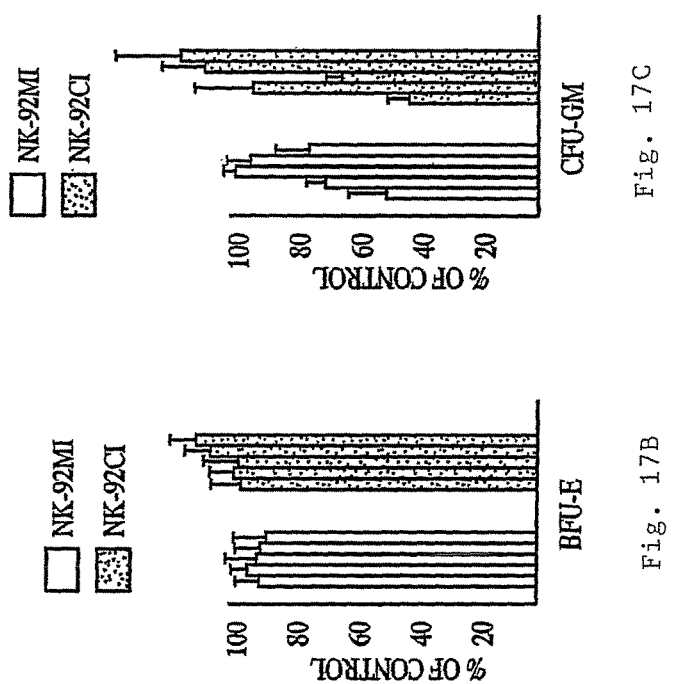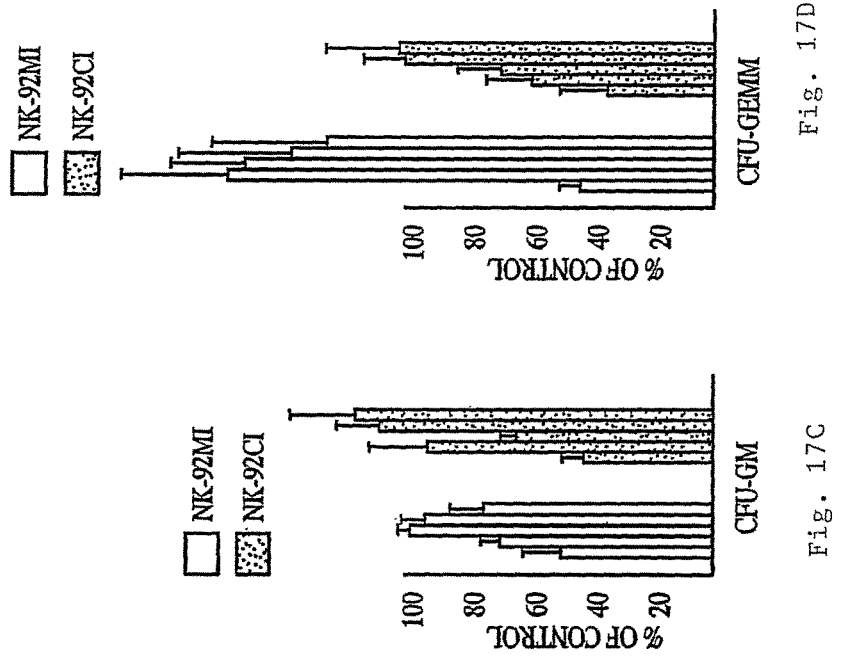

NATURAL KILLER CELL LINES AND METHODS OF USE

RELATED APPLICATION

This is a continuation-in-part of U.S. patent application Ser. No. 09/403,910 filed Oct. 27, 1999 (now abandoned), which was a nationalized application of PCT Application No. PCT/US98/08672 filed Apr. 30, 1998, which claims priority to U.S. Provisional Patent Application No. 60/045,885 filed Apr. 30, 1997.

FIELD OF THE INVENTION

This invention relates to natural killer cells and their use in the treatment of pathologies related to cancer or viral infections. Specifically, a particular cell line, NK-92, and modifications thereof, are disclosed. These cells are shown to be highly effective in the treatment of these pathologies.

BACKGROUND OF THE INVENTION

Certain cells of the immune system have cytotoxic activity against particular target cells. Cytotoxic T lymphocytes (CTLs) are specifically directed to their targets via antigen-derived peptides bound to MHC class !-specific markers. Natural killer (NK) cells, however, are not so restricted. NK cells, generally representing about 10-15% of circulating lymphocytes, bind and kill target cells, including virus-infected cells and many malignant cells, nonspecifically with regard to antigen and without prior immune sensitization (Herberman et al., *Science* 214.24 (1981)). Killing of target cells occurs by inducing cell lysis. MHC class restriction likewise is not involved. In these ways the activity of NK cells differs from antigen-specific and MHC class-specific T cells, such as cytotoxic T lymphocytes. Use of NK cells in the immunotherapy of tumors and malignancies is suggested by these properties, since many tumors are MHC class I deficient and therefore do not attract CTL activity. Adhesion molecules may also be involved in the targeting of NK cells; for example, it is observed that the Fcγ receptor (CD16) is expressed on NK cells. NK cells are large granular lymphocytes which lack CD3, and in addition to CDI6, also may express Leu19 (Lanier et al., *J. Immunol.* 136; 4480 (1986)).

NK cells are activated when exposed to cytokines such as interleukin-2 (IL-2), IL-7, IL-12, and interferons (Alderson et al., *J. Exp. Med.* 172:577-587 (1990); Robertson et al., *J. Exp. Med.* 175:779-788 (1992)). The resulting cells are called lymphokine activated killer (LAK) cells. The spectrum of target cells is altered in activated NK cells compared to nonactivated cells, although the mechanism of killing may be identical or similar (Philips et al., *J. Exp. Med.* 164:814-825 (1986)).

More generally, killing activity in the cells of the immune system may be induced by treating a population of cells, such as peripheral blood mononuclear cells (PBMCs), with lymphokines. Such preparations contain LAK cells. LAK cells may also be generated from autologous samples of peripheral blood lymphocytes. LAK cells have antitumor killing activity while having essentially no effect on normal cells. They appear to purge leukemia (Long et al., *Transplantation* 46:433 (1988); Xhou et al., *Proc. Am. Assoc. Cancer Res.* 34:469 (1993; abstract)), lymphoma (Schmidt-Wolf et al., *J. Exp. Med.* 174: 139 (1991); Gambacorti-Passerini et al., *Br. J. Haematol.* 18:197 (1991)) and neuroblastoma (Ades et al., *Clin. Immunol. Immunopathol.* 46:150 (1988)). NK cells, activated NK cells, and LAK cells are distinguishable by their cell surface markers and by the identity of the target cells that they kill.

Activated and expanded (i.e., cultured to proliferate) NK cells and LAK cells have been used in both ex vivo therapy and in vivo treatment in patients with advanced cancer. Some success with ex vivo therapy has been observed in bone marrow related diseases, such as leukemia, breast cancer and certain types of lymphoma. In vivo treatment may be directed toward these and other forms of cancer, including malignant melanoma and kidney cancer (Rosenberg et al., *N. Engl. J. Med.* 316:889-897 (1987)). LAK cell treatment requires that the patient first receive IL-2, followed by leukophoresis and then an ex vivo incubation and culture of the harvested autologous blood cells in the presence of IL-2 for a few days. The LAK cells must be reinfused along with relatively high doses of IL-2 to complete the therapy. This purging treatment is expensive and can cause serious side effects. These include fluid retention, pulmonary edema, drop in blood pressure, and high fever. In some cases in which these side effects occur, intensive care unit management is required.

Purging techniques have been applied in other circumstances as well. Cytotoxic drugs or monoclonal antibodies combined with complement, and toxins, may be administered in order to bring about remission. In such cases bone marrow or blood stem cells, purged to reduce the number of residual leukemic cells present, have been infused back into the patient after the drug treatment (Uckun et al., *Blood* 79:1094 (1992)). Gene marking studies have shown that unpurged bone marrow may contribute to relapse in patients presumed to be in remission (Brenner et al., *Lancet* 341:85 (1993)). This suggests that some form of purging of autologous marrow or blood prior to transplantation is necessary (Klingemann et al., *Biol. Blood Marrow Transplant.* 2:68-69 (1996)).

Recently, preclinical studies have also demonstrated promising antitumor activity in vivo with a lethally irradiated, MHC-unrestricted, cytotoxic T-cell leukemic clone (TALL-104) (Cesano et al., *Cancer Immunol. Immunofher.* 40:139-151 (1995); Cesano et al., *Blood* 87:393-403 (1996)). These cells were derived from leukemia T cell lines obtained from patients having acute T lymphoblastic leukemias (ALL). They bear the CD3 cell surface marker, but not the CD56 marker, in distinction to NK cells which have the converse immunophenotype (CD3$^-$ CD56$^+$). Adoptive transfer of these cells was able to eliminate human leukemic cell lines in xenografted severe combined immunodeficient (SCID) mice and to induce remissions of spontaneous lymphomas in dogs without producing T-cell leukemia in the animal models (Cesano et al. (1995); Cesano et al. (1996); Cesano et al., *J. Clin. Invest.* 94:1076-1084 (1994); Cesano et al., *Cancer Res.* 56:3021-3029 (1996)).

In spite of the advantageous properties of NK cells in killing tumor cells and virus-infected cells, they remain difficult to work with and to apply in immunotherapy. It is difficult to expand NK cells ex vivo that maintain their tumor-targeting, tumoricidal, and viricidal capabilities in vivo. This remains a major obstacle to their clinical use in adoptive cell immunotherapy (Melder et al., *Cancer Research* 48:3461-3469 (1988); Stephen et al., *Leuk. Lymphoma* 377-399 (1992); Rosenberg et al., *New Engl. J. Med.* 316:889-897 (1987)). Studies of the mechanisms whereby NK cells exert their tumoricidal and viricidal effects are also limited by difficulties in enriching the NK cell fractions without compromising their biological functions and in obtaining pure NK cells that are not contaminated by T cells or other immune effector cells. In an attempt to overcome these problems, many investigators have turned to the use of established NK-like cell lines to explore the mechanisms whereby target cells are susceptible to cytotoxic cells (Hercend et al., *Nature* 301:158-160 (1983); Yodoi et al., *J. Immunol.* 134:1623-1630 (1985); Fernandez et al., *Blood* 67:925-930 (1986); Robertson et al., *Exp. Hematol.* 24:406-415 (1996); Gong et al., *Leukemia* 8:652-658 (1994)). NK cell lines described in earlier work carry T lymphocyte-associated surface markers, in spite of the fact that they were developed from precursor cells depleted of T cells (Rosenberg, et al. (1987); Hercend, et al., (1983)).

There thus remains a need for a method of treating a pathology related to cancer or a viral infection with a natural killer cell line that maintains viability and therapeutic effectiveness against a variety of tumor classes. This need encompasses therapeutic methods in which samples from a mammal are treated ex vivo with natural killer cells, as well as methods of treatment of these pathologies with natural killer cells in vivo in a mammal. There is also a need for a natural killer cell line that maintains its own propensity for viability and cytolytic activity by secreting a cytokine which fosters these properties. There also remains a need for such natural killer cell lines which are modified to be more effective, convenient, and/or useful in treatment of cancer and viral infection. It is the objective of this invention to provide NK cells and methods that address these needs.

SUMMARY OF THE INVENTION

The cell line described by Gong et al. (1994), termed NK-92, proliferates in the presence of IL-2 and has high cytolytic activity against a variety of cancers. The present invention employs the NK-92 cell line, as well as modified NK-92 cell lines, to provide cancer treatment and virus treatment systems. The invention also provides the vectors that transfect NK-92, as well as the modified NK-92 cells. For purposes of this invention and unless indicated otherwise, the term "NK-92" is intended to refer to the original NK-92 cell lines as well as the modified NK-92 cell lines disclosed herein.

One aspect of the invention provides a vector for transfecting NK-92 cells, wherein the vector includes a nucleic acid sequence encoding a protein that is either a cytokine which promotes the growth of the NK-92 cells, a cellular component responsive to an agent, a cancer cell receptor molecule, or any combination of these proteins. When transfected with the vector, the NK-92 cells constitutively express the protein. In an important embodiment, the protein is the cytokine interleukin 2. In especially important embodiments of this aspect of the invention, the vectors are MFG-hIL-2 and pCEP4-LTRhIL-2. In additional significant embodiments, the protein is a cellular component responsive to an agent, such that when the vector transfects NK-92 cells and the agent is taken up by the cells, the cells are inactivated. In still more significant embodiments the agent is either acyclovir or gancyclovir. A further embodiment of the invention provides a cell population containing NK-92 cells that have been modified by a physical treatment or by transfection with a vector.

In significant embodiments of this population, the physical treatment renders them non-proliferative yet does not significantly diminish the cytotoxicity of the cells, and in particularly significant embodiments, the treatment is irradiation. In additional important embodiments the cells have been transfected by a vector that encodes a cytokine promoting the growth of the cells. The cells secrete the cytokine both upon being cultured under conditions that promote cytokine secretion or in vivo upon being introduced into a mammal. In particularly important embodiments of this aspect of the invention, the cytokine is interleukin 2. In still further important embodiments, the NK-92 cells are the cells NK-92MI, modified by transfection with the vector MFG-hIL-2 encoding interleukin-2, and the cells NK-92CI modified by transfection with the vector pCEP4-LTRhIL-2 encoding interleukin-2. The NK-92MI cell line was deposited into the general depository of the American Type Culture Collection (ATCC), 10801 University Blvd., Manassas, Va. 20110-2209, on Sep. 3, 1998, was assigned ATCC Deposit No. CRL-2408, was moved to the patent depository on Apr. 4, 2005, and was assigned Deposit No. PTA-6671. The NK-92CI cell line was deposited into the general depository of ATCC on Sep. 3, 1998, was assigned ATCC Deposit No. CRL-2409, was moved to the patent depository on Apr. 4, 2005, and was assigned ATCC Deposit No. PTA-6672. In additional important embodiments, the NK-92 cells are transfected by a vector including a sequence that encodes a cellular component responsive to an agent such that, when the NK-92 cell so transfected takes up the agent, the cell is inactivated. In particularly important embodiments thereof, the agent is acyclovir or gancyclovir. In yet additional embodiments, the cell population is transfected with a vector encoding a cancer cell receptor molecule.

The present invention also provides a method of purging cells related to a pathology from a biological sample including the steps of (i) obtaining a biological sample from a mammal that is suspected of containing cells related to the pathology, and (ii) contacting the sample with a medium comprising NK-92 or modified NK-92 natural killer cells, wherein the modified NK-92 cells have been modified by a physical treatment or by transfection with a vector. In significant embodiments of this method, the pathology is a cancer, or is an infection by a pathogenic virus such as human immunodeficiency virus (HIV), Epstein-Barr virus (EBV), cytomegalovirus (CMV), or herpes virus. In additional important embodiments, the modified NK-92 cells have undergone a physical treatment that renders them non-proliferative, yet which does not significantly diminish their cytotoxicity, or have been transfected with a vector, or they have been treated by any combination of these modifications. In significant embodiments of this method, the vector encodes a cytokine that promotes the growth of the cells, a protein that is responsive to an agent, a cancer cell receptor molecule, or a combination of these coding sequences. In a further embodiment, the medium also includes a cytokine that promotes the growth of the cells. The sample, once purged of cancer cells, may be further treated, including, for example, being returned to the mammal from which it was obtained. In important embodiments of the method, the biological sample is blood or bone marrow, the mammal is a human, and/or the natural killer cell is immobilized on a support.

The invention additionally provides a method of treating a pathology ex vivo in a mammal including the steps of (i) obtaining a biological sample suspected of containing cells related to the pathology from the mammal; (ii) contacting the biological sample with a medium including natural killer cells, either NK-92 cells or modified NK-92 cells that have been modified by a physical treatment or by transfection with a vector, thereby selectively destroying the cells related to the pathology in the sample and producing a purged sample, and (iii) returning the purged sample to the mammal. The pathology may be a cancer, such as a leukemia, a lymphoma, or a multiple myeloma. Alternatively, the pathology may be infection by a pathogenic virus such as HIV, EBV, CMV, or herpes. In this method the natural killer cells may be NK-92 itself or modified NK-92 cells. Examples of such modified NK-92 cells include those that have been modified by a physical treatment that renders them non-proliferative yet does not significantly diminish their cytotoxicity, and modification by transfection with a vector. The vector encodes a cytokine that promotes the growth of the cells, or a protein that is responsive to an agent, or a cancer cell receptor molecule, or the vector may include any combination of these modifications. In important embodiments of this method, the biological sample is blood or bone marrow, the mammal is a human, and/or the natural killer cell is immobilized on a support. In additional significant embodiments, the medium further includes a cytokine that promotes the growth of the cells, and/or the cancer is a leukemia, a lymphoma or a multiple myeloma.

The present invention further provides a method of treating a pathology in vivo in a mammal including the step of administering to the mammal a medium comprising natural killer cells, either NK-92 cells or NK-92 cells that have been modified by a physical treatment that renders them non-proliferative yet does not significantly diminish their cytotoxicity, by treatment that inhibits expression of HLA antigens on the NK-92 cell surface, or by transfection with a vector. The vector encodes a cytokine that promotes the growth of the cells, or a protein that is responsive to an agent, or a cancer cell receptor molecule, or they have been treated by any combination of these modifications. In important embodiments, the pathology is a cancer, such as a leukemia, a lymphoma, or a multiple myeloma. Alternatively, in important embodiments the pathology is infection by a pathogenic virus such as HIV, EBV, CMV, or herpes. Advantageous embodiments of this method include administering the cells intravenously to a human and administering a cytokine that promotes the growth of the cells to the mammal in conjunction with administering the medium comprising the natural killer cell. The present methods are especially adapted for the treatment of leukemia, lymphoma or multiple myeloma.

In yet an additional embodiment of the in vivo method of treating cancer, the NK-92 is modified by transfection with a vector comprising an element responsive to an agent such that when the agent is taken up by the cell, the cell is inactivated. According to this method, an amount of the agent effective to inactivate the cell can be administered to a mammal after a time sufficient for the natural killer cell to treat the cancer has elapsed or at a time desirable to effectively end the treatment. A significant aspect of this embodiment is one in which the agent is acyclovir or gancyclovir. Such transfected cells can, in effect, be "turned off" as desired by administering the agent.

Mice in the indicated groups received rhIL-2 every other day for two weeks.

Figure 13:
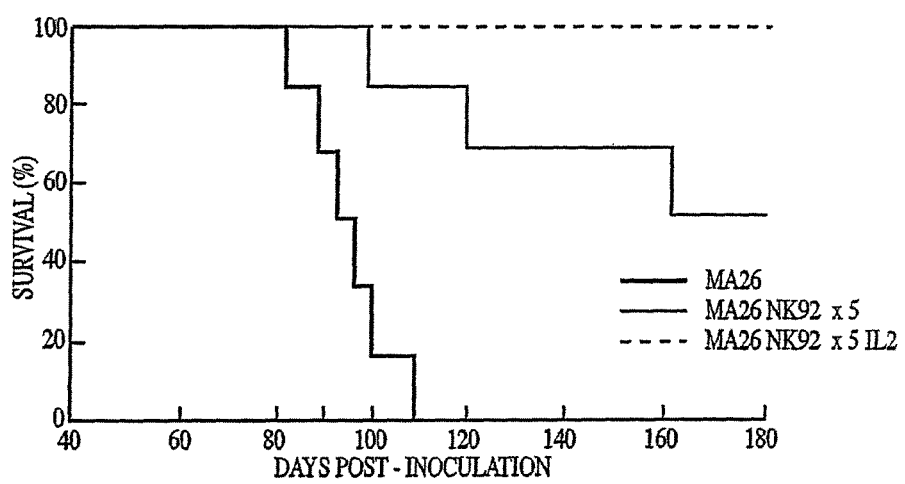

FIG. 13. Survival of SCID mice bearing human AML (MA26) after treatment with NK-92 cells. Mice received $5 \times 10^6$ MA26 leukemia cells I.P. NK-92 ($2 \times 10^7$) cells were injected I.P. on days 1, 3, 5, 7 and 9 for a total of five doses. Mice in the indicated groups received rhIL-2 every other day for two weeks.

Figure 14:
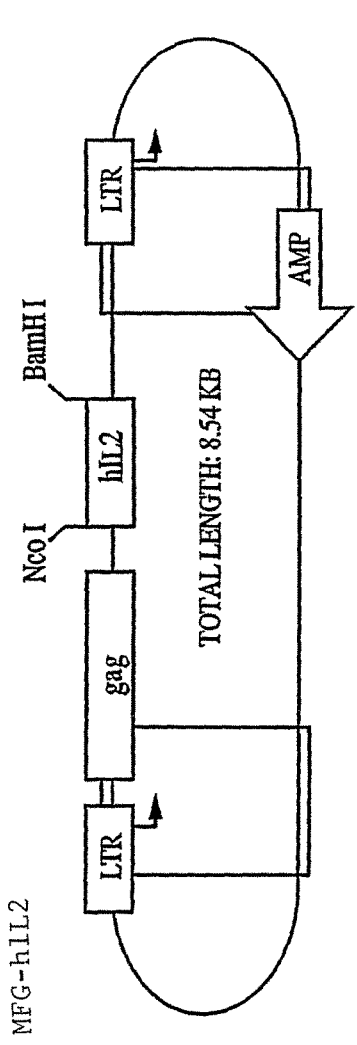

FIG. 14. Diagrammatic map of plasmid MFG-hIL-2.

Figure 15:
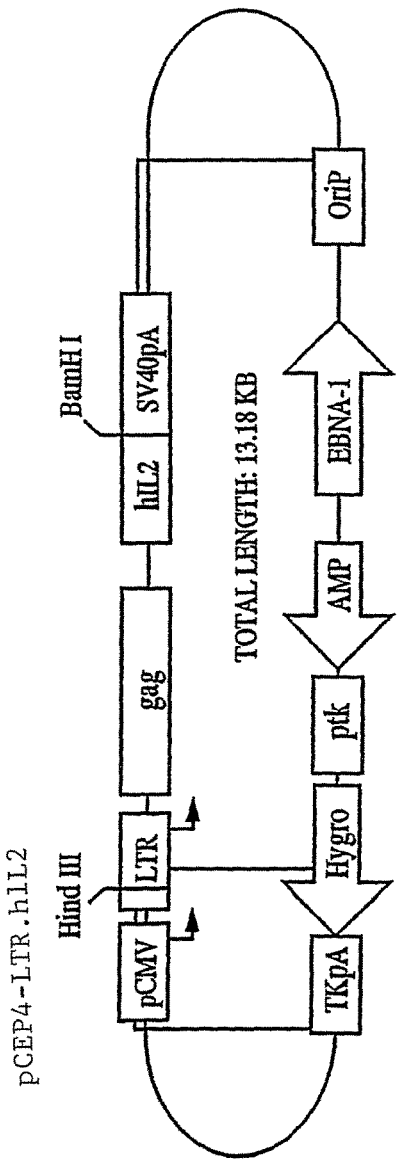

FIG. 15. Diagrammatic map of plasmid pCEP4-LTR.hIL-2.

Figure 16B:
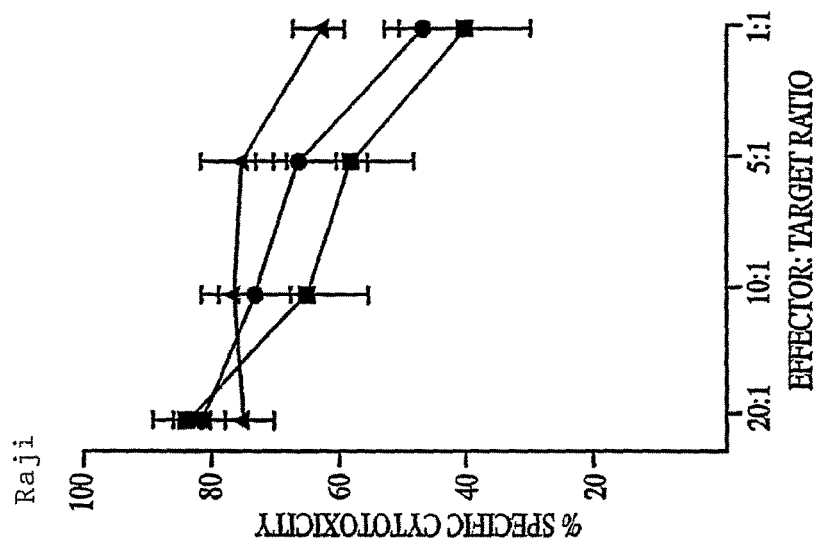
Figure 16A:

FIG. 16. Cytotoxicity of NK-92, NK-92MI and NK-92CI against K562 and Raji target cells. The cytotoxic activities of the IL-2 transfectants were compared to that of the parental cell line. NK cells were mixed with $^{51}$Cr-labeled K562 (Panel A) or Raji (Panel B) cells at effector:target ratios of 1:1, 5:1, 10:1 and 20:1 for a 4 hour chromium release assay. The cytotoxicities of NK-92 (•), NK-92MI (▲) and NK-92CI (■) are shown.

FIG. 17. Effect of NK-92 MI and NK-92CI on hematopoietic progenitors. To assay the effect of the NK-92 cells on normal hematopoietic progenitors, a clonogenic assay was performed. Normal PBMCs were incubated with irradiated NK-92MI or NK-92CI at various NK:PBMC ratios ranging from 1:1 to 1:1000 for 48 hours. The cells were plated in methylcellulose at concentrations to give 10-100 colonies per dish after 14 days. Clonogenic output of PBMCs incubated with NK-92MI (white bars) and NK-92CI (gray bars) is expressed as either total number of colonies or subclassified on the basis of colony type (BFU-E, CFU-GM and CFU-GEMM).

Figure 18A:
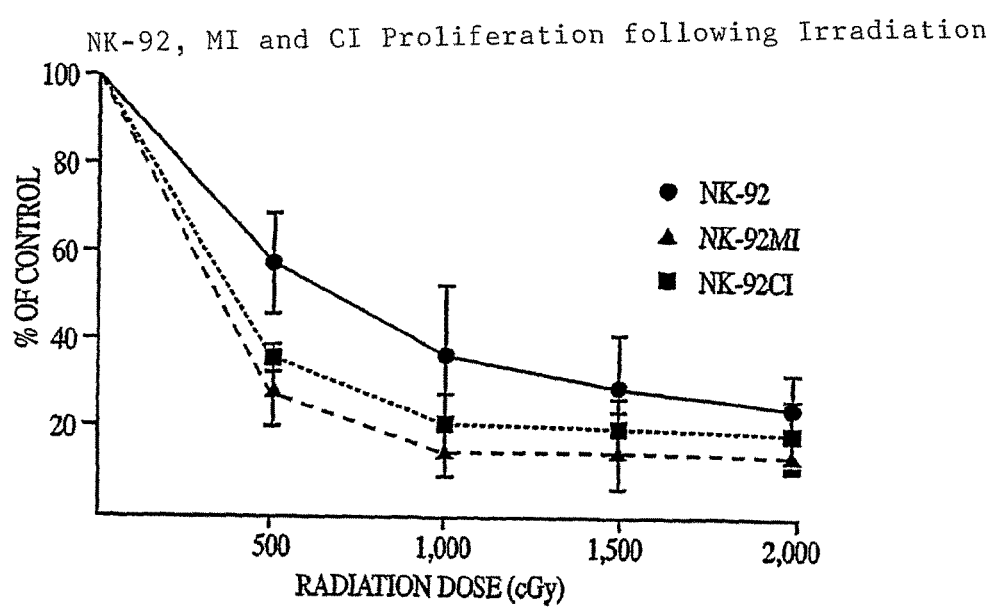
Figure 18B:
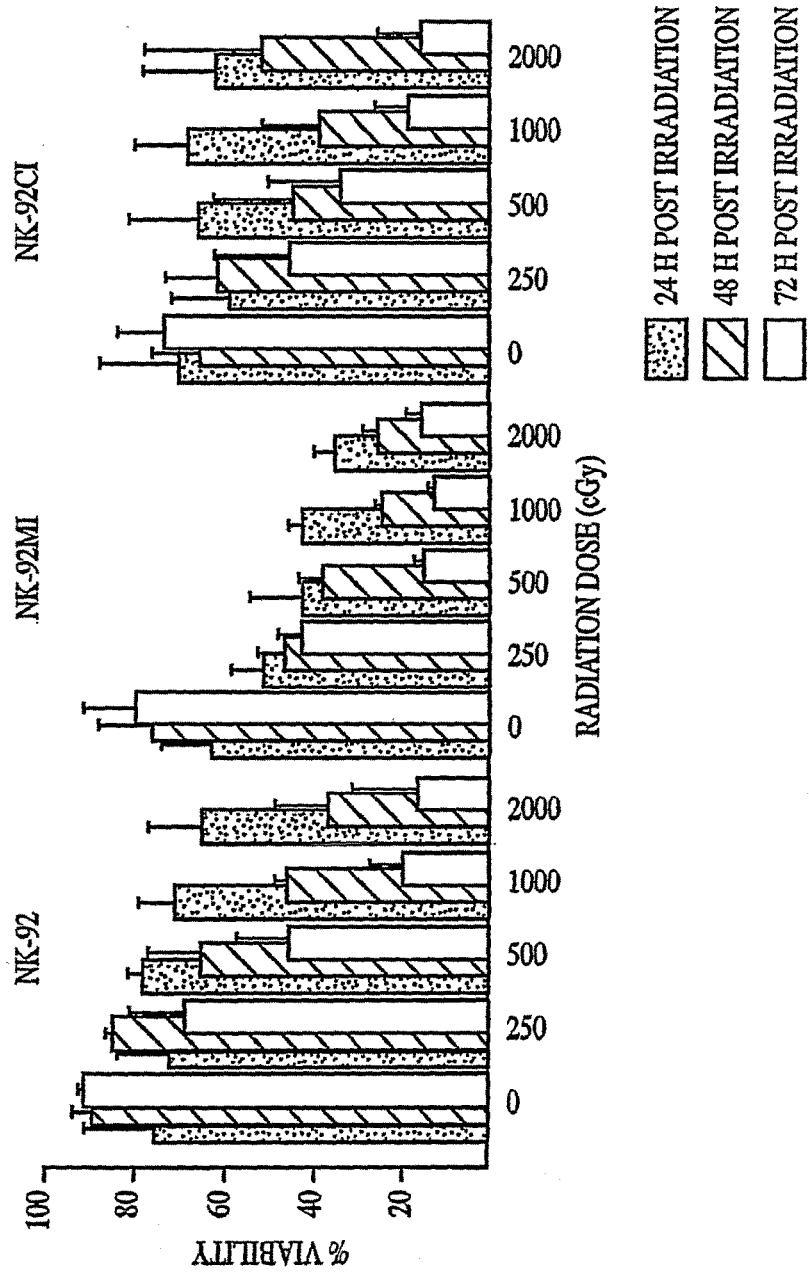

FIG. 18. Effect of irradiation on NK-92, NK-92MI and NK-92CI proliferation and viability. To assess the effect of irradiation on the parental and transfected NK-92 cells, cells were exposed to 0, 500, 1,000, 1,500, and 2,000 cGy doses of radiation and assayed for proliferation by a standard $^3$H-thymidine incorporation assay. Panel A: Proliferation of NK-92 (•), NK-92MI (▲) and NK-92CI (■) is expressed as a percentage of control (unirradiated cells). Panel B: Cells were exposed to 0, 250, 500, 1,000, and 2,000 cGy of irradiation and assessed by trypan blue exclusion for viability after 24 (black bars), 48 (gray bars) and 72 hours (white bars).

Figure 19A:
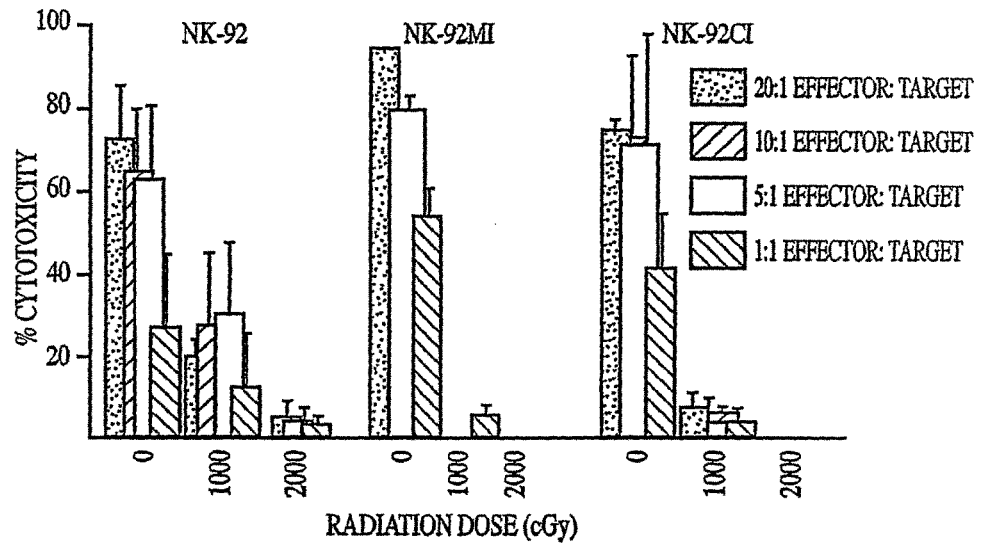
Figure 19B:
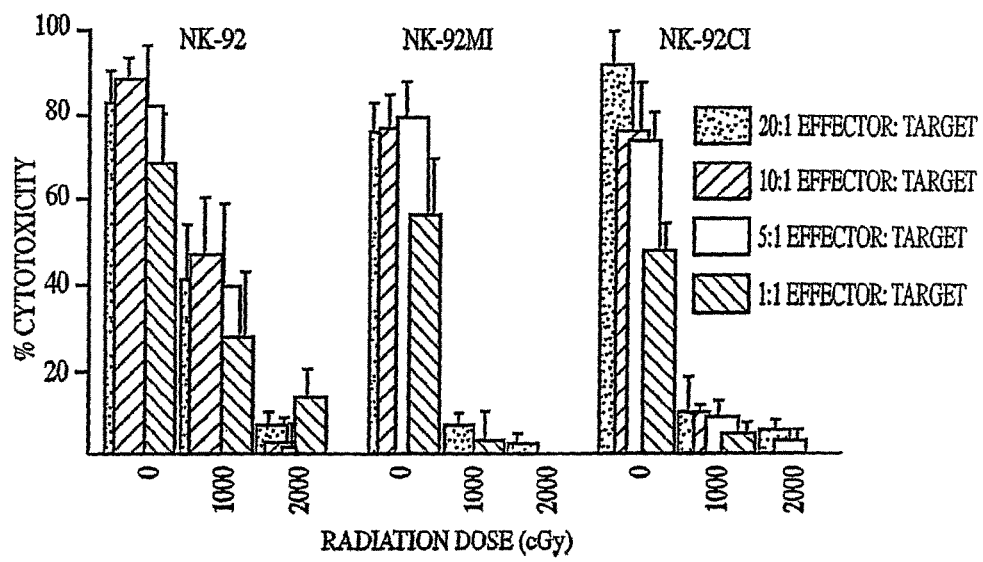

FIG. 19. Effect of irradiation on NK-92, NK-92MI and NK-92CI cytotoxicity. To assess the effect of irradiation on cytotoxicity of the NK cells, NK-92, NK-92MI and NK-92CI were irradiated at 0, 1,000, and 2,000 cGy and tested after three days for cytotoxicity against K562 (Panel A) and Raji (Panel B) cells.

DETAILED DESCRIPTION OF THE INVENTION

The present invention relates to methods of treating a biological sample or a mammal suspected of having a pathology such as a cancer or an infection by a virus. Certain natural killer cells which are cytolytic for the cells affected by the pathology are employed. The treatment results in significant diminution of the number, or, in some cases, the elimination, of malignant or cancerous cells, or virus-infected cells, in the sample or mammal. The natural killer cells of this invention are designated NK-92 cells and include certain treated or transfected modifications of NK-92 cells. These cells are highly effective in purging cancer cells ex vivo and in destroying cancer cells in vivo.

As used in the present invention, "cytotoxic T lymphocytes" (CTL) relate to immune cells which kill antigen-specific target cells. CTL are MHC class I-restricted. As used in the present invention, lymphokine activated killer (LAK) cells relate to cells of the immune system that have antitumor killing activity. They are obtained from a population of cells, such as peripheral blood mononuclear cells, upon activation by treatment with lymphokines. LAK cells have essentially no effect on normal cells.

As used to describe the present invention, "natural killer (NK) cells" are cells of the immune system that kill target cells in the absence of a specific antigenic stimulus, and without restriction according to MHC class. Target cells may be tumor cells or cells harboring viruses. NK cells are characterized by the presence of CD56 and the absence of CD3 surface markers. The present invention is based on an immortal NK cell line, NK-92, originally obtained from a patient having non-Hodgkin's lymphoma. As used to describe the present invention, a modified NK-92 cell is an NK-92 cell which has been further treated to endow it with properties not found in the parent from which it is derived. Such treatments include, for example, physical treatments, chemical and/or biological treatments, and the like. The treatments confer properties upon the modified NK-92 cells that render them more advantageous for the purposes of the invention.

As used to describe the present invention, the terms "cytotoxic" and "cytolytic", when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

As used to describe the present invention, "target cells" are the cells that are killed by the cytotoxic activity of the NK cells of the invention. These include in particular cells that are malignant or otherwise derived from a cancer, and cells that are infected by pathogenic viruses such as HIV, EBV, CMV, or herpes.

As used to describe the present invention, "purging" relates to killing of target cells by effector cells such as NK cells ex vivo. The target cells may be included in a biological sample obtained from a mammal believed to be suffering from a pathology related to the presence of the target cell in the sample. The pathology may be a cancer or malignancy due to tumor cells in the sample, and may be treated by purging the sample of the tumor cells and returning the sample to the body of the mammal.

As used to describe the present invention, "inactivation" of the NK-92 cells renders them incapable of growth and/or their normal function, in particular, their cytotoxic activity. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of nonlimiting example, by administering an inactivating agent to which the NK-92 cells are sensitive.

As used herein, a "vector" relates to a nucleic acid which functions to incorporate a particular nucleic acid segment, such as a sequence encoding a particular gene, into a cell. In most cases, the cell does not naturally contain the gene, so that the particular gene being incorporated is a heterologous gene. A vector may include additional functional elements that direct and/or regulate transcription of the inserted gene or fragment. The regulatory sequence is operably positioned with respect to the protein-encoding sequence such that, when the vector is introduced into a suitable host cell and the regulatory sequence exerts its effect, the protein is expressed. Regulatory sequences may include, by way of non-limiting example, a promoter, regions upstream or downstream of the promoter such as enhancers that may regulate the transcriptional activity of the promoter, and an origin of replication. A vector may additionally include appropriate restriction sites, antibiotic resistance or other markers for selection of vector containing cells, RNA splice junctions, a transcription termination region, and so forth.

As used to describe the present invention, "cancer", "tumor", and "malignancy" all relate equivalently to a hyperplasia of a tissue or organ. If the tissue is a part of the lymphatic or immune system, malignant cells may include non-solid tumors of circulating cells. Malignancies of other tissues or organs may produce solid tumors. In general, the methods of the present invention may be used in the treatment of lymphatic cells, circulating immune cells, and solid tumors.

As used to describe the present invention, a "pathogenic virus" is a virus causing disease in a host. The pathogenic virus infects cells of the host animal and the consequence of such infection is a deterioration in the health of the host. Pathogenic viruses envisioned by the present invention include, but are not limited to, HIV, EBV, CMV, and herpes.

Natural Killer Cell NK-92.

The NK-92 cell line has been described by Gong et al. (1994). It is found to exhibit the $CD56^{bright}$, CD2, CD7, CD11a, CD28, CD45, and CD54 surface markers. It furthermore does not display the CD1, CD3, CD4, CD5, CD8, CD10, CD14, CD16, CD19, CD20, CD23, and CD34 markers. Growth of NK-92 cells in culture is dependent upon the presence of recombinant interleukin 2 (rIL-2), with a dose as low as 10 IU/mL being sufficient to maintain proliferation. IL-7 and IL-12 do not support long-term growth, nor do other cytokines tested, including IL-1α, IL-6, tumor necrosis factor α, interferon α, and interferon γ. NK-92 is highly effective in killing certain tumor cells, such as K562 (erythroleukemia) and Daudi (Burkitt lymphoma) cells, for it has high cytotoxicity even at a low effector:target (E:T) ratio of 1:1 (Gong et al. (1994)). In addition, NK-92 cells have high cytotoxic activity against 8E5 cells, which are infected with HIV and produce HIV virions. NK-92 cells were deposited into the general despository of the American Type Culture Collection (ATCC), 10801 University Blvd., Masassas, Va. 20110-2209, on Sep. 3, 1998, was assigned ATCC Deposit No. CRL-2407, was moved to the patent depository on Apr. 4, 2005, and was assigned ATCC Deposit No. PTA-6670.

NK-92 cells are readily maintained in culture medium, such as enriched alpha minimum essential medium (MEM; Sigma Chemical Co., St. Louis, Mo.) supplemented with fetal calf serum (for example, at 12.5%; Sigma Chemical Co., St. Louis, Mo.), and horse serum (for example, at 12.5%; Sigma Chemical Co., St. Louis, Mo.). Initially, $10^6$ M hydrocortisone is required, but in subsequent passages it is found that hydrocortisone may be omitted. In addition, IL-2, such as recombinant human IL-2 (500 U/mL; Chiron, Emeryville, Calif.), is required for long-term growth. When suspension cultures are maintained in this fashion with semiweekly changes of medium, the cells exhibit a doubling time of about 24 h.

NK-92 cells in vitro demonstrate lytic activity against a broad range of malignant target cells. These include cell lines derived from circulating target cells such as acute and chronic lymphoblastic and myelogenous leukemia, lymphoma, myeloma, melanoma, as well as cells from solid tumors such as prostate cancer, neuroblastoma, and breast cancer cell lines. This effect is observed even at very low effector:target ratios. This lysis is superior to cytotoxicity obtained from normal peripheral blood mononuclear cells stimulated for four days with IL-2.

Vector for Transfecting Mammalian Cells to Produce Cytokine.

The present invention provides NK-92 cells which have been modified by transfection with a vector that directs the secretion of a cytokine, such as IL-2. In order that NK-92 cells maintain long-term growth and cytolytic function, they generally must be supplied with IL-2. A vector encoding the gene for human IL-2, and which also contains a control element directing the synthesis of the IL-2 gene product is therefore of great utility in the invention. NK-92 cells bearing such a vector secrete the IL-2 needed for cytolytic activity in a therapeutic setting; thus, IL-2 from an exogenous source is not required. The control element is one which directs the synthesis of IL-2 as a constitutive product, i.e., one that is not dependent upon induction. Methods for constructing and employing vectors are described in general terms in "Current Protocols in Molecular Biology", Ausubel et al., John Wiley and Sons, New York (1987, updated quarterly), and "*Molecular Cloning: A Laboratory Manual 2nd Ed.*", Sambrook, Fritsch and Maniatis, Cold Spring Harbor Laboratory, Cold Spring Harbor, N.Y. (1989), which are incorporated herein by reference.

Modified NK-92 Transfected to Produce Cytokine, and Method of Transfecting.

Modified NK-92 cells that secrete a cytokine may be prepared by inserting a vector that directs the synthesis and secretion of the cytokine into the cells. In important aspects of the invention, the cytokine is IL-2. Methods of introducing a vector into a mammalian cell are well known to workers of ordinary skill in molecular biology and cellular immunology, and are described in Ausubel et al. (1987, updated quarterly) and Sambrook et al. (1989). The vectors encoding the cytokine encompass as well control elements that lead to constitutive synthesis of the cytokine when incorporated into the NK-92 cells.

When cultured under appropriate conditions that promote cytokine secretion the transfected NK-92 cells secrete IL-2 or other cytokine. Since the vector directs constitutive synthesis of the cytokine, nutrient cultures in which the NK-92 cells are known to grow and to exhibit their normal cytolytic function are sufficient for the transfected cells to secrete the cytokine. For the same reason, the transfected cells secrete the cytokine in vivo when they are introduced within the body of a mammal.

NK-92 cells transfected with a vector that directs secretion of a cytokine such as IL-2 are useful in the ex vivo treatment of a biological sample drawn from a mammal which is suspected of containing malignant cells. By treating the malignant cells with these modified NK-92 cells, the need for applying exogenous IL-2 or other cytokine is obviated. These modified NK-92 cells are useful, for the same reasons, in the in vivo treatment of a mammal suffering from a malignancy. The modified NK-92 cells exert their cytolytic effect against the malignant cells when introduced into the body of the mammal. Examples of such cells in the present invention are designated NK-92MI and NK-92CI.

NK-92 Cells that are Cytolytic but not Capable of Proliferation.

An additional modified NK-92 cell of the invention is one that has been treated in such a way that it is no longer able to proliferate, yet whose cytotoxic activity is preserved. One way of achieving this state is by $\gamma$ irradiation. Additional forms of radiation, including, for example, ultraviolet radiation, may be employed. Suitable sources to use for this purpose include, for example, a $^{137}Cs$ source (Cis-US, Bedford, Mass.; Gammacell 40, Atomic Energy of Canada Ltd., Canada). Additionally, proliferative activity may be abrogated by treatment with chemical agents which inhibit DNA synthesis. An example of such an agent is mitomycin C.

Vector for Transfecting NK-92 with an Element Responsive to an Inactivating Agent.

The NK-92 cells may also be modified by transfection with a vector such that, when the cell takes up a specific agent, the cell is inactivated. The vector includes a sequence that encodes a cellular component responsive to the agent, such that when the vector transfects a cell and the agent is taken up by the cell, the cell is inactivated. In preferred embodiments, the agent is acyclovir or gancyclovir. The vector also contains a control element directing the synthesis of the cellular component as a constitutive product.

The NK-92 cell transfected with the vector described in the preceding paragraph maintains its characteristic growth and cytolytic activity in the absence of the agent. At a point in time, for example, when an ex vivo sample has been purged of malignant cells by the action of the NK-92 cells, or when the NK-92 cells administered in vivo have effectively exerted their cytolytic activity within a mammalian body, or when it desired that the treatment be stopped for any reason, the agent may be administered. The agent interacts with the cellular component sensitive to the agent encoded in the vector. The interaction of the agent with the cellular component induces the inactivation of the NK-92 cells. Inactivation may range from loss of characteristic cytolytic function to death of the cells.

This property of the modified NK-92 cells is significant because the parent NK-92 cells are derived from a tumor cell line that may continue propagating in a sample reintroduced into a mammal after ex vivo therapy, or in vivo when so administered. It is therefore important to ablate the cells after they have carried out their therapeutic function. Rendering the cells sensitive to an agent such as acyclovir or gancyclovir is an advantageous way of achieving this objective.

Vector for Transfecting NK-92 with an Altered HLA Cell Surface Molecule.

The HLA cell surface protein, involved in presenting antigens to other cells of the immune system, includes a non-immunospecific subunit, the protein $\beta_2$-microglobulin. If this protein is altered or mutated, the HLA protein loses its affinity for the T-cell receptor to which it ordinarily binds. The $\beta_2$-microglobulin gene in NK-92 cells of the invention may be mutated by site specific mutagenesis in order to transform its properties in this way. The result is an NK-92 cell which no longer has a high affinity for T-cell receptors. As a result, the NK-92 cell modified in this way remains within the host organism for a longer period of time, rather than being eliminated by the action of the host's cellular immune response.

Vector for Transfecting NK-92 with a Gene Encoding a Cancer Cell Receptor Molecule.

The NK-92 cells may also be modified by transfection with a vector such that the cells constitutively express a receptor for a cancer cell. Cancer cells express cell surface molecules that are idiosyncratic for the origin of the cancer, and frequently are also idiosyncratic for the individual host. The CTL population in such diseased patients may have been activated by exposure to the cells of the growing cancer. Such activated CTL express cell surface proteins that are specific for, or target, the cells of the cancer. These CTL may be isolated, the gene for the targeting receptor identified, isolated, and transfected into the NK-92 cells of the invention. This confers on the NK-92 cells the capability of likewise specifically targeting the cancer cells present in the individual host. This has the effect of enhancing the specificity of the cytotoxic activity of the NK-92 cells toward the cancer cells of that individual. The corresponding process would be carried out for each host suffering from cancer, taking advantage of the idiosyncratic specificity of the CTL targeting moiety in each case.

Methods of Treating.

The natural killer cells of the invention are employed in methods of treating biological samples in order to purge them of cells from a cancer, a malignancy, or a tumor, or cells infected by a pathogenic virus. The NK cells include by way of nonlimiting example, NK-92, and modified NK-92 cells, such as NK-92MI and NK-92CI, as well as other modified NK-92 cells envisioned within the scope of this invention. The NK-92MI and NK-92CI cells are modified by transfection with vectors that result in the secretion of IL-2. In addition, any of the NK-92, NK-92MI, and NK-92CI cells may be treated such that they maintain the cytolytic activity of the untreated cells but cannot proliferate. The NK cells so treated may also be equivalent cell lines which have the properties such as cytotoxicity and NK-specific cell surface markers described herein. Malignancies of the immune system, the lymphatic system, and the hematopoietic system may be treated by the methods of the invention. In addition, formed tumors and solid tumors may also be treated. Infections by pathogenic viruses, such as HIV, EBV, CMV, and herpes may also be treated.

Treating a Biological Sample.

In vitro biological samples may be treated experimentally or therapeutically in order to eliminate malignant cells, or virus-infected cells, in an effective manner. The sample may be drawn from a mammal and maintained in vitro in an appropriate culture medium. Such media are well known to workers of skill in cell biology, cellular immunology, and oncology. Media and cell culture techniques are presented in general terms in, for example, Freshney, R. I., "Culture of Animal Cells, 3rd Ed.", Wiley-Liss, New York (1994), and in Martin, B. M., "Tissue Culture Techniques, An Introduction", Birkhauser, Boston, Mass. (1994), which are incorporated herein by reference. The biological sample is established in culture in vitro, and contacted with a medium that includes the natural killer cells of the present invention. The cytolytic activity of the NK cells effectively eliminates the malignant cells or the virus-infected cells from the sample. The prevalence and depletion of the target cells may be traced by any of a number of methods well known to those of skill in the fields of cell biology and cellular immunology.

These include indirect immunofluorescence microscopy to assay for intact tumor cells or virus-bearing cells, fluorescent-activated cell sorting, chromium release assays, and the like.

Treating a Cancer or Virus Infection Ex Vivo: Purging.

The present invention additionally encompasses the ex vivo treatment of a biological sample suspected of containing cancer cells or virus-infected cells by contacting the sample with the NK cells of the invention. The biological sample is drawn from the body of a mammal, such as a human, and may be blood, bone marrow cells, or similar tissues or cells from an organ afflicted with a cancer. Methods for obtaining such samples are well known to workers in the fields of cellular immunology, oncology, and surgery. They include sampling blood in well known ways, or obtaining biopsies from the bone marrow or other tissue or organ. The cancer cells or virus-infected cells contained in the sample are effectively eliminated due to the cytotoxic activity of the NK-92 cells. The sample may then be returned to the body of the mammal from which it was obtained.

The NK-92 cells used to treat the sample, may be freely suspended in the medium. It is generally preferred that the purged sample, prior to being returned to the body of the mammal from which it was obtained, be rid of NK-92 cells that may continue growing, since they arose originally from a proliferating lymphoma. The invention envisions several ways of accomplishing this objective. In one embodiment, the NK cells, prior to use, are irradiated with γ rays or with ultraviolet light to the extent that they maintain their cytolytic activity but are not capable of growth. In an additional embodiment, the NK cells are permanently immobilized on a macroscopic solid support. The support with the NK cells attached may then be physically separated from the cells of the biological sample, for example by centrifugation, or filtration with a column which permits the unbound cells of the sample to pass through, or like technique. Suitable solid supports include particles of polyacrylamide, agarose, cellulose, Sepharose™ (Pharmacia, Piscataway, N.J.), celite, and the like, and may be supplied with groups such as an aldehyde, carbonyldiimidazole, broamoacetyl, epichlorhydrin, and the like, which are activated for reaction with cell surface groups. The activated groups on the support react with groups such as amino or carboxyl groups, for example, on the cell surface, thereby immobilizing the cells on the support.

In yet a further embodiment, the NK cells may be modified with a vector directing the synthesis of a cellular component sensitive to an agent, such that when the agent is administered to the ex vivo sample, the NK-92 cells are inactivated. Examples of such agents include acyclovir or gancyclovir, by way of nonlimiting example. Functionally equivalent vectors, directing the synthesis of alternative cellular components sensitive to different agents, are also envisioned within the scope of this embodiment.

The NK cells to be used in the methods of the invention may require a cytokine such as IL-2 to maintain their functional effectiveness as cytolytic cells. The cytokine may simply be added to the ex vivo preparation. Alternatively, if desired, a modified NK-92 cell bearing a vector directing the constitutive synthesis of the cytokine may be employed. In this way the necessity of furnishing exogenous cytokine is avoided.

Treating a Cancer or Virus Infection In Vivo: Administering NK-92.

A further method of the invention is directed toward treatment of a cancer or a virus infection in vivo in a mammal using NK-92 cells. The cells are administered in a variety of ways. By way of nonlimiting example, the cells may be delivered intravenously, or into a body cavity adjacent to the location of a solid tumor, such as the intraperitoneal cavity, or injected directly within or adjacent to a solid tumor. Intravenous administration, for example, is advantageous in the treatment of leukemias, lymphomas, and comparable malignancies of the lymphatic system, as well as in the treatment of viral infections.

As has been described in detail in the preceding section, it is desirable to employ methods that eliminate or ablate the NK-92 cells after they have effectively lysed (or otherwise destroyed) the target cells. Certain methods described above may be employed for this purpose, namely, use of irradiated NK-92 cells, and use of NK-92 cells harboring a vector directing the synthesis of a cellular component sensitive to an agent, such that when the agent is administered, the NK-92 cells are inactivated, and equivalent methods. When the cells produce such a component sensitive to the specific agent, administration of the agent to the mammal is effective to inactivate the NK-92 cells within the mammal.

The NK-92 cells may be administered in conjunction with a cytokine such as IL-2 in order to maintain the functional effectiveness of the cells as cytotoxic effectors. As used to describe the invention, the term "in conjunction" indicates that the cytokine may be administered shortly prior to administration of the NK-92 cells, or it may be given simultaneously with the cells, or shortly after the cells have been administered. The cytokine may also be given at two such times, or at all three times with respect to the time of administering the NK-92 cells. Alternatively, NK-92 cells harboring a vector directing the constitutive synthesis of the cytokine may be employed in the in vivo method of treating a cancer. This effectively eliminates the need to furnish exogenous cytokine.

The following examples are included to illustrate the invention and not to limit the invention. All publications or references cited in the present specification are hereby incorporated by reference.

EXAMPLES

Example 1. NK-92 Cells

NK-92 cells (Gong et al. (1994)) were derived from cells obtained from a patient suffering from non-Hodgkin's lymphoma. PBMC from the patient were cultured in enriched alpha MEM supplemented with fetal calf serum (12.5%) and horse serum (12.5%) plus $10^{-6}$M hydrocortisone and 1000 U/mL of recombinant human IL-2 (rhIL-2). Cells were cultured at 37° C. in humidified air containing 5% $CO_2$. Subcultures were made after 4 weeks, and propagated indefinitely with twice-weekly changes in medium. In these later stages the hydrocortisone could be omitted without any effect on cell growth. This culture has been designated NK-92 and has been deposited with the American Type Culture Collection (ATCC; Rockville, Md.) under designation CLR-2407.

The cells have the morphology of large granular lymphocytes. The cells bear the $CD56^{bright}$, CD2, CD7, CD11a, CD28, CD45, and CD54 surface markers. In contrast, they do not display the CD1, CD3, CD4, CD5, CD8, CD10, CD14, CD16, CD19, CD20, CD23, and CD34 markers. Growth of NK-92 cells in culture is dependent upon the presence of recombinant interleukin 2 (IL-2), with a dose as low as 10 IU/mL being sufficient to maintain proliferation. IL-7 and IL-12 do not support long-term growth, nor do other cytokines tested, IL-1α, IL-6, tumor necrosis factor α, interferon α, and interferon γ.

Example 2. Cytotoxic Activity of NK-92 Against Different Leukemic Cell Lines

The cytotoxic activity of NK-92 against K562, Daudi, TF-1, AML-193, and SR-91 cells was determined (Gong et al. (1994)). K562 (erythroleukemia) and Daudi (Burkitt) lymphoma cell lines were obtained from ATCC. They were maintained in continuous suspension culture in RPMI 1640 medium supplemented with 10% fetal calf serum (FCS). TF-1 is a myelomonocytic cell line (Kitamura et al., *J. Cell Physiol.* 140:323-334 (1989)) that requires the presence of medium containing 2 ng/mL of human GM-CSF. AML-193 is a myeloid cell line that is maintained in the presence of 10% 5637-conditioned medium (Lange et al., Blood 70:192-199 (1987)). Both TF-1 and AML-193 cells were obtained from Dr. D. Hogge, Terry Fox Laboratory, University of British Columbia, Vancouver, BC. SR-91 is a cell line with features of early progenitor cells established by Gong et al. (1994) from a patient with acute lymphoblastic leukemia (ALL) (Klingemann et al., *Leuk. Lymphoma*, 12, 463-470 (1994). It is resistant to both NK and activated-NK (A-NK) cell cytotoxicity. SR-91 is also maintained in RPMI 1640/ 10% FCS. This cell line can be rendered sensitive to killing by NK-92 by treatment with cytokine. Naki et al., "Induction of sensitivity to the NK-mediated cytotoxicity by TNF-α treatment: Possible role of ICAH-3 and CD44," *Leukemia*, in press.

The cytotoxic activity of NK-92 (effector) against these target cells was assessed by means of a $^{51}$Cr release assay (Gong et al. (1994)) using the procedure described by Klingemann et al. (*Cancer Immunol. Immunother.* 33:395-397 (1991)). The percentage of specific cytotoxicity in triplicate specimens was calculated as:

$$\% \ ^{51}Cr \ \text{release} = \frac{(\text{average experimental } cpm - \text{average spontaneous } cpm)}{(\text{average maximum } cpm - \text{average spontaneous } cpm)} \times 100$$

Figure 1:
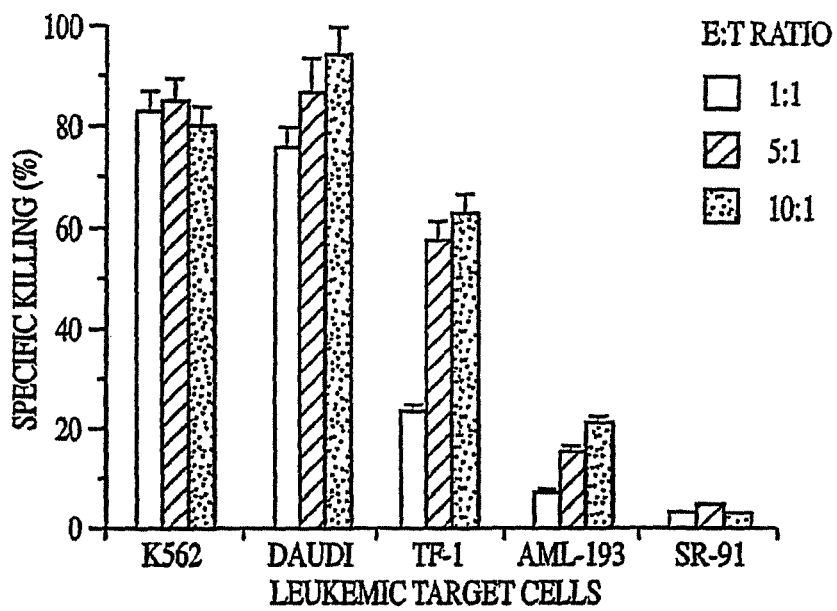
FIG. 1. Cytotoxic activity of NK-92 against different leukemic target cell lines tested in a 4 hour $^{51}$Cr release assay. The results represent the mean±the standard deviation (SD) for three replicate experiments.

FIG. 1 presents the results of this determination. It is seen that NK-92 cells kill K562 and Daudi cells with high efficiency. Even at the low E:T ratio of 1:1, 83% of K562 cells and 76% of Daudi cells were killed by NK-92 cells. Susceptibility to killing by NK-92 cells was lower for TF-1. cells (23% at E:T=1:1) and for AML-193 cells (6% at E:T=1:1). SR-91 cells appear to be resistant to the cytotoxic effect of the NK-92 cells. Without wishing to be bound by theory, it is believed that SR-91 cells lack adhesion molecules necessary to mediate initial binding with NK-92 cells.

Example 3. Cytotoxicity of NK-92 Against Leukemia, Lymphoma, and Myeloma Target Cell Lines K562 (Ph-chromosome positive [Ph*] erythroleukemia), HL60 (promyelocytic), U937 (myelomonocytic), KG1 a (variant subline of the AML cell line KG1), DHL-10 (B-cell lymphoma), Daudi (Burkitt's lymphoma), Raji (B-cell lymphoma), Jurkat (T-cell lymphoma), 0266 (IgE myeloma), NCI H929 (IgA myeloma), and RPMI 8226 (myeloma, light chain secreting) cell lines were obtained from ATCC. The lymphoma-derived cell lines Ly3 (B-lineage, diffuse large cell), Ly8 (immunoblastic), and Ly13.2 (T-lineage, diffuse large cell) were provided by Dr. H. Messner, Toronto, Ontario. Their characteristics have been described (Chang et al., *Leuk. Lymphoma* 19:165 (1995)). All lines were maintained in RPM1 1640 medium supplemented with 2 mM glutamine, 1 mM sodium pyruvate, 0.1 mM nonessential amino acids, 50 U/mL penicillin, 25 mM HEPES (StemCell Technologies), and 5% heat-inactive FCS (RPMI/5% FCS) at 37° C. in a humidified atmosphere of 5% $CO_2$ in air.

Cell lysis was determined by a 4-hour $^{51}$Cr release assay using various E:T ratios. To allow for comparison, PBMCs from normal donors were activated with IL-2 (500 U/mL) for 4 days and $^{51}$Cr release measured against the same target cells concurrently. The mean of two separate experiments is presented.

Results of NK-92-mediated cytotoxicity ("Cr release assay) against various leukemia, lymphoma, and myeloma target cell lines are summarized in Table 1. For comparison, lysis of the same tumor target cells was also tested in the same experiment with PBMCs obtained from normal donors. Those cells had been activated by IL-2 (500 U/mL) for 4 days prior to testing. Results show that NK-92 cells very effectively lyse all target cells tested. High cytotoxicity is observed even at the low E:T ratio of 1:1. The cytotoxicity achieved with these cells is significantly higher than that observed with normal (allogeneic) PBMCs activated under optimal conditions with IL-2 for all the target cells except RPMI 8226 and 0266.

TABLE 1

Cytotoxic activity of NK-92 cells against various leukemia, lymphoma, and myeloma cell lines

| Target | | 50:1 | 20:1 | 10:1 | 5:1 | 1:1 |
|---|---|---|---|---|---|---|
| HL-60 | NK-92 | 97 | 90 | 77 | 46 | 40 |
|  | PBMCs + IL-2 | 31 | 26 | 17 | 2 | 0 |
| K562 | NK-92 | 68 | 68 | 64 | 59 | 50 |
|  | PBMCs + IL-2 | 63 | 73 | 67 | 51 | 19 |
| KG1a | NK-92 | 90 | 91 | 80 | 67 | 39 |
|  | PBMCs + IL-2 | 15 | 11 | 12 | 6 | 0 |
| U937 | NK-92 | 99 | 98 | 96 | 91 | 85 |
|  | PBMCs + IL-2 | 57 | 43 | 23 | 13 | 2 |
| DHL-10 | NK-92 | 95 | 95 | 92 | 94 | 80 |
|  | PBMCs + IL-2 | 60 | 40 | 24 | 19 | 5 |
| Daudi | NK-92 | 94 | 87 | 71 | 48 | 39 |
|  | PBMCs + IL-2 | 65 | 57 | 29 | 16 | 6 |
| Jurkat | NK-92 | 100 | 100 | 98 | 93 | 80 |
|  | PBMCs + IL-2 | 67 | 50 | 36 | 27 | 4 |
| Ly 3 | NK-92 | 63 | 59 | 53 | 42 | 28 |
|  | PBMCs + IL-2 | 47 | 35 | 18 | 6 | 095 |
| Ly 8 | NK-92 | 95 | 104 | 102 | 88 | 42 |
|  | PBMCs + IL-2 | 67 | 65 | 62 | 59 | 44 |
| Ly 13.2 | NK-92 | 104 | 105 | 100 | 97 | 67 |
|  | PBMCs + IL-2 | 61 | 63 | 52 | 4 | 13 |
| Raji | NK-92 | 81 | 75 | 74 | 70 | 54 |
|  | PBMCs + IL-2 | 32 | 67 | 57 | 35 | 13 |
| NCI H929 | NK-92 | 94 | 89 | 89 | 86 | 51 |
|  | PBMCs + IL-2 | 75 | 58 | 39 | 24 | 5 |
| RPMI 8224 | NK-92 | 82 | 72 | 70 | 72 | 41 |
|  | PBMCs + IL-2 | 95 | 83 | 81 | 67 | 25 |
| U266 | NK-92 | 84 | 77 | 85 | 81 | 53 |
|  | PBMCs + IL-2 | 84 | 74 | 73 | 56 | 21 |

Example 4. Effect of Deprivation of IL-2 on Cytotoxic Activity of NK-92

Figure 2:
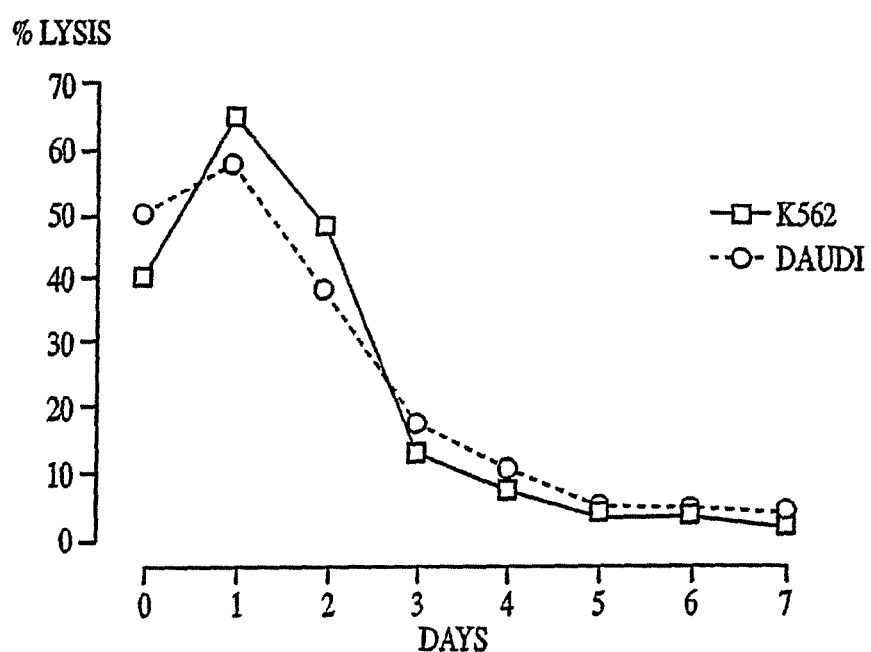
FIG. 2. Cytotoxicity of NK-92 after IL-2 deprivation. NK-92 cells were cultured in enriched alpha medium (Myelocult™, StemCell Technologies, Vancouver, BC) without IL-2. Cytotoxicity was measured daily with the $^{51}$Cr-release assay against K562-neo' or Daudi target cells. The Figure shows results from one representative experiment at the E:T ratio of 10:1.

To test how long NK-92 cells would maintain their cytolytic activity without IL-2 present in the culture medium, NK-92 cells were deprived of IL-2 and $^{51}$Cr-release was measured in 24-hour intervals. Results, summarized in FIG. 2, suggest that the cells maintain full cytotoxic activity for at least 48 hours. Thereafter, the activity drops precipitously to negligible levels. Thus, for short-term purging, IL-2 does not have to be present in the cultures to achieve a suitable effect.

Example 5. Co-Culture of K562-Neo' Cells with PBMC's and NK-92

The transfection of the K562 cells with the neomycin-resistance (neo') gene has been described (Wong et al., *Bone Marrow Transplant* 18:63 (1966)). Briefly, $5 \times 10^7$ K562 cells were suspended in 0.8 mL RPMI 1640/5% FCS and incubated on ice for 10 minutes with 30 μg of the pMCI-Neo plasmid (provided by Dr. K. Humphries, Terry Fox Laboratory, Vancouver, BC). The cells were then exposed to a single voltage pulse (125 μF/0.4 kV) at room temperature, allowed to remain in buffer for 10 minutes, transferred into 25-cm² tissue culture flasks (Falcon, Lincoln Park, N.J.), and incubated at 37° C. in a humidified atmosphere of 5% $CO_2$ in air for 2 days. Transfected cells were selected in 0.8% Iscove's methylcellulose medium (StemCell Technologies) supplemented with 30% FCS, $10^{-4}$ M 2-mercaptoethanol, and 2 mM glutamine, containing 0.8 mg/mL G418 (neomycin) (Gibco-BRL, Grand Island, N.Y.). Neo' clones of K562 cells were identified after 2 weeks, plucked, and maintained in RPMI/10% FCS containing 0.8 mg/mL neomycin. K562-neo' cells cultured for 2 days showed a neo' clonogenic cell doubling time of 36-42 hours.

Normal PBMCs ($10^4$/mL) were spiked with 10% K562-neo' cells, and NK-92 cells were added to yield different effector:target (E:T) ratios of NK-92:K562-neo' cells. (Wong et al. (1996)). Briefly, PBMCs were suspended in enriched alpha medium (Myelocult™) as described above. This medium has been shown to provide optimal conditions for supporting both IL-2 activation of PBMCs and hematopoietic progenitor cell function (Klingemann et al., *Exp. Hematol.* 21:1263 (1993)). The final concentration of PBMCs in 35-mm tissue culture dishes (Corning, East Brunswick, N.J.) was $1 \times 10^6$/mL, and the proportion of input K562-neo' cells was kept at 10% for all experiments. Various numbers of irradiated (1000 cGy) NK-92 cells (see Examples 7 and 8) were added, resulting in various E:T ratios as specified in Table 2. These mixtures were cultured in an atmosphere of 5% $CO_2$ in air for 4 or 48 hours at 37° C. with and without IL-2 (500 units/mL).

After the culture, cells were washed in RPMI/5% FCS, $10^3$ cells were suspended in 0.8% Iscove's methylcellulose containing 0.8 mg/mL neomycin, and 1.1-mL volumes were plated in 3-mm petri dishes. After 7 days at 37° C. in a humidified atmosphere of 5% $CO_2$ in air, colonies were counted. The number of neo' colonies provided a measure for the number of surviving clonogenic K562-neo' cells present in the cell suspension originally plated. Percent survival values for co-cultures containing various numbers of NK-92 cells were determined by comparing the number of clonogenic K562-neo' cells present in test co-cultures with the number of those present in control co-cultures (no NK-92 cells added) and harvesting after the same period of incubation. At an input number of $10^3$ K562-neo' cells prior to purging, the absolute number of clonogenic K562-neo' cells after 4 hours with no NK-92 cells present was 6400±820 cells and after 48 hours 28,300±2100 cells. The mean±SEM of four to eight experiments is reported.

When only PBMCs were plated in the neomycin-containing methylcellulose medium, no colonies were ever observed. To quantitate the purging capacity of NK-92 cells, PBMCs were spiked with 10% K562-neo' cells and cultured for 4 or 48 hours in medium in the presence or absence of IL-2. Results, summarized in Table 2, show that NK-92 cells used at E:T ratios of 10:1 and 5:1 eliminated the K562-neo' cells from PBMCs, and that very low survival was observed at E:T of 1:1. The presence of IL-2 during the purging did not result in any increase in the number of K562 cells purged compared to no IL-2 (Table 2).

TABLE 2

| Purging effect of NK-92 cells | | | | |
|---|---|---|---|---|
| NK-92:K562-neo' | % Survival (−IL-2) of K562-neo' | | % Survival (+IL-2) of K562-neo' | |
| E:T Ratio | 4 hrs. | 48 hrs. | 4 hrs. | 48 hrs. |
| 10:1 | 0 | 0 | 0 | 0 |
| 5:1 | 0 | 0 | 0 | 0 |
| 1:1 | 10.5 ± 2.1 | 15.4 ± 7.2 | 6.5 ± 3 | 15.2 ± 5.9 |
| 0.1:1 | 56 ± 14.1 | 68.5 ± 19.5 | 54.4 ± 13 | 69.6 ± 16.8 |

Example 6. Effect of NK-92 Cells on Hematopoietic Progenitor Cells

The effect of NK-92 cells on PBMCs was determined (Cashman et al., *Blood* 75:96 (1990)). Briefly, normal PBMCs were co-cultured with irradiated (1000 cGy) NK-92 cells (see Examples 7 and 8) for 2 days. Cells were then plated in replicate 1.1-mL aliquots of methylcellulose-containing media at densities adjusted to give approximately 10-100 large colonies of erythroid cells (from burst-forming units-erythroid [BFU-E]), granulocytes and macrophages (from colony-forming units-granulocyte/macrophage [CFU-GM]), and combinations of all of these (from CFU granulocyte/erythroid/macrophage/megakaryocyte [CFU-GEMM]). Colonies were counted under an inverted microscope 2 weeks later.

The number and growth kinetics of clonogenic hematopoietic cells were quantified at a 1:1 ratio of NK-92: PBMC after 2 days of co-culture with irradiated (1000 cGy) NK-92 cells. The cells were plated in standard methylcellulose and counted 2 weeks later. Results obtained from three different normal donors are presented as percentage of normal controls in Table 3. No growth inhibitory effect on hematopoietic progenitors by NK-92 cells was noted.

TABLE 3

| Effect of NK-92 cells on colony formation of normal hematopoietic progenitor cells. | | | |
|---|---|---|---|
| Experiment Number | CFU-GEMM | BFU-E | CFU-C |
| 1 | 100 | 46 | 94 |
| 2 | 200 | 98 | 64 |
| 3 | 33 | 104 | 103 |

Example 7. γ-Irradiation of NK-92 Cells

NK-92 cells were irradiated in T25 flasks (Corning, Newark, N.J.) with the dose indicated using a cesium source (Cis-US, Bedford, Mass.). A dose range of 200-2000 cGy was tested. After irradiation, the cells were washed twice in RPMI, resuspended in medium, and cultured for 72 hours at 37° C. in the presence of 500 IU/mL IL-2. Cytotoxicity ($^{51}$Cr-release assay) was performed with these cells as described above in Example 2. Prior to performing the $^{51}$Cr-release assay, the cells were left for 24 hours in medium supplemented with IL-2 to allow for recovery. Proliferation was assessed by means of a $^3$H-thymidine incorporation assay. Prior to adding $^3$H-thymidine (0.5 µCi/cell), NK-92 cells were resuspended in thymidine-free RPMI. Uptake of $^3$H-thymidine was measured in a liquid scintillation counter 4 hours later. (Klingemann et al., Leuk. Lymphoma 12:463 (1994)). The counts per minute (cpm) from three different experiments are presented.

Figure 3:
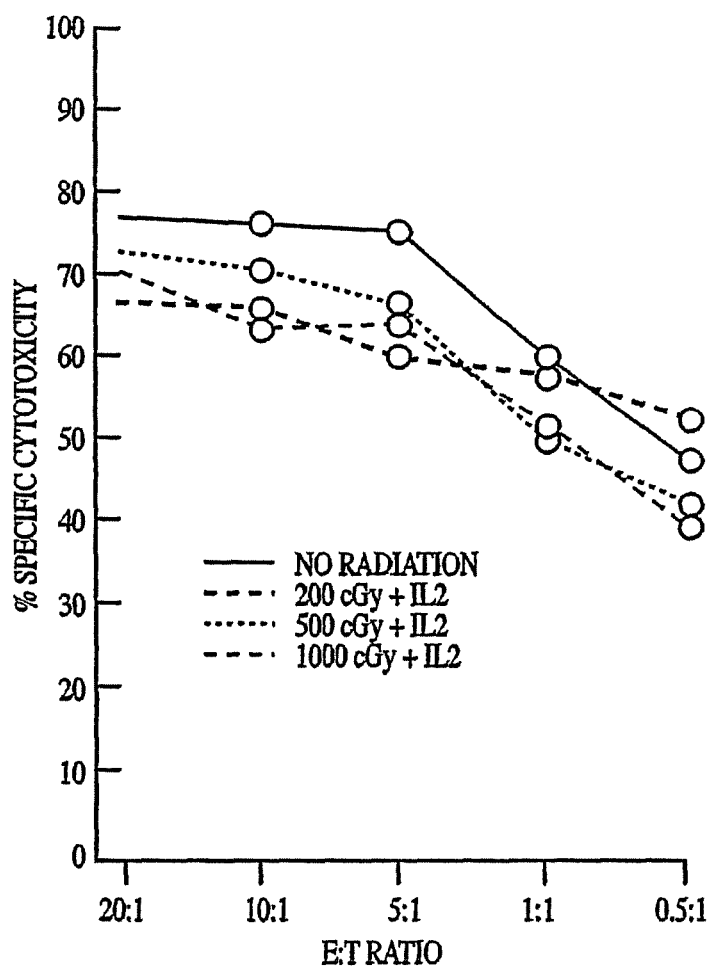
FIG. 3. Effect of various doses of γ radiation on the cytolytic potential of NK-92 cells. NK-92 cells were irradiated with a $^{137}$Cs source using doses ranging from 200 to 1000 cGy. To allow for recovery, cells were left in medium containing IL-2 for 24 hours before cytotoxicity was measured in a 4 hour $^{51}$Cr release assay against the target cell line K562.

Clinical use of this cell line to purge cancerous cells requires that NK-92 cells not undergo significant growth and proliferation. This was achieved by irradiating the cells. Proliferation, as measured by $^3$H incorporation, was effectively reduced at a dose of 1000 cGy (Table 4). The cytotoxicity of NK-92 cells after administration of various radiation doses is presented in FIG. 3. At doses up to 1000 cGy an essentially undiminished cytolytic response was maintained.

TABLE 4

Effect of irradiation on the proliferation of NK-92 cells

| Experiment Number | Radiation dose (cGy) | | | | |
|---|---|---|---|---|---|
| | 0 | 500 | 1000 | 1500 | 2000 |
| 1 | 5766 | 3071 | 406 | 125 | 114 |
| 2 | 4236 | 2411 | 1216 | 1192 | 562 |
| 3 | 3894 | 2046 | 824 | 689 | 748 |

Example 8. Radiation Susceptibility of NK-92 Cells

NK-92 cells were irradiated by a γ ray source (Gammacell 40, Atomic Energy of Canada. Ltd., Canada). A dose range of 100-3000 cGy was tested. After irradiation, the cells were washed and resuspended in culture medium with rhIL-2. Colony assays, viability and cytotoxic activity of the irradiated NK-92 cells were performed using standard techniques (Yan et al., Leukemia, 7:131-139 (1993)). To quantify clonogenic NK-92 cells, NK-92 cells (500 cells per mL culture medium) were cultured in a 0.3% agar-based medium supplemented with 12.5% FCS, 12.5% horse serum, 2 mM L-glutamine, 100 µg/mL penicillin 50 µg/mL streptomycin, 10$^{-5}$ M mercaptoethanol, and 500 U/mL rhIL-2 at 37° C. for 14 days. An additional aliquot of 500 U/mL rhIL-2 was added at day 7 during the culture. Triplicate cultures were performed for each data point.

Figure 4:
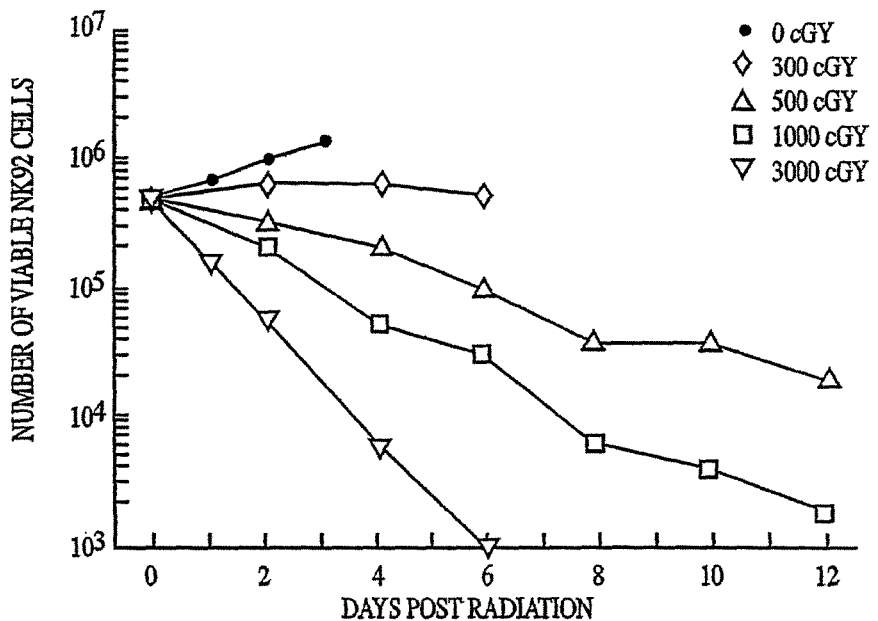
FIG. 4. Survival curves of NK-92 cells after γ-irradiation. NK-92 cells were irradiated with a γ ray source at doses of 300, 500, 1000, and 3000 cGy. Viability of NK-92 cells was determined by trypan blue staining. The maximal achievable concentration of the non-irradiated NK-92 cells in culture was about 1.5×10$^6$/mL. The cells had to be fed to prevent overgrowth.
Figure 5:
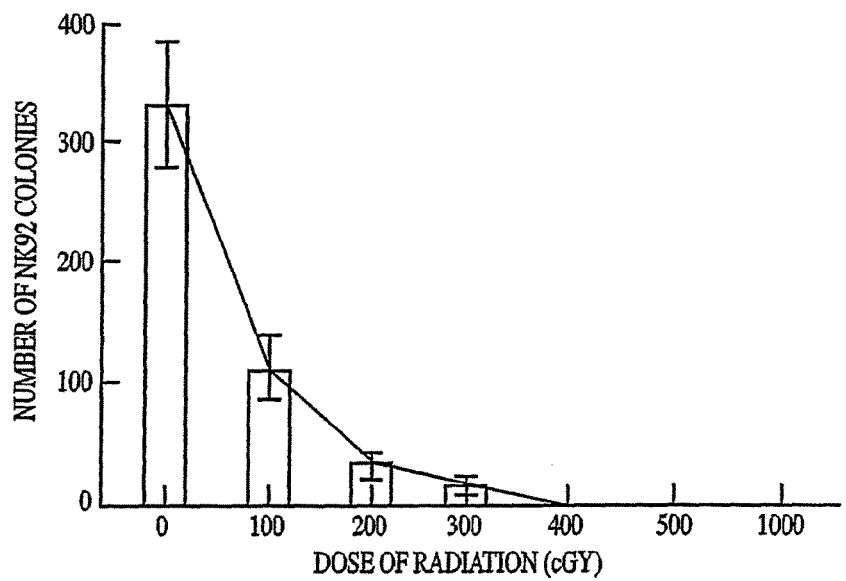
FIG. 5. Effect of γ-irradiation on the in vitro colony formation of NK-92 cells. NK-92 cells were cultured in agar-based medium supplemented with recombinant human IL-2 (rhIL-2).
Figure 6A:
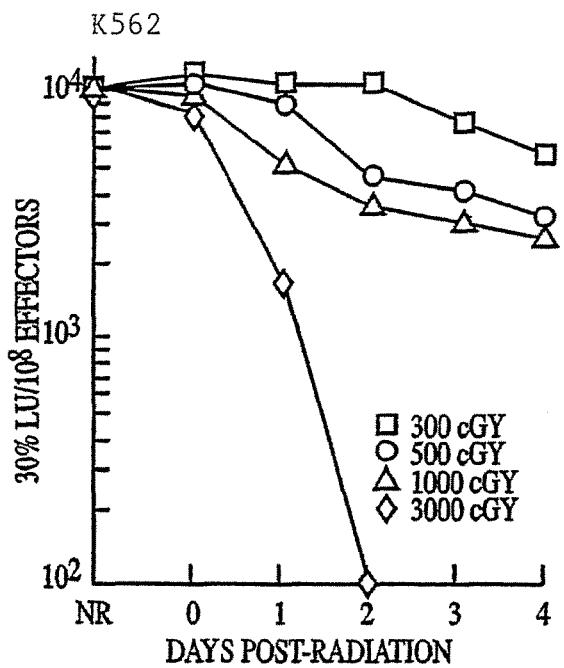
FIG. 6. Effect of various radiation doses on the cytolytic potential of NK-92 cells. NK-92 cells were γ-irradiated at doses of 300, 500, 1000, and 3000 cGy. $^{51}$Cr-labeled leukemic target cells K562 (Panel A) and HL60 (Panel B) as well as two patient-derived leukemic samples TA27 (Panel C) and BA25 (Panel D) were tested for susceptibility to cytolysis by irradiated and non-irradiated (NR) NK-92 cells. The results of 4 hr chromium release assays are expressed as 30% lytic units/10$^8$ effector cells.
Figure 6B:
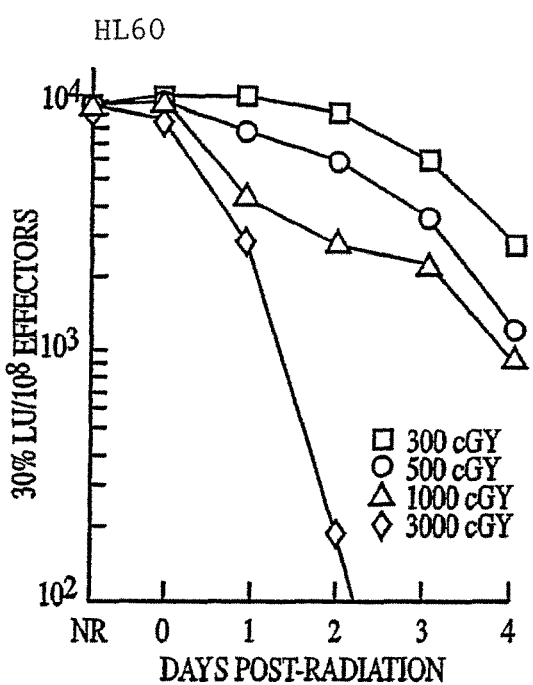
Figure 6C:
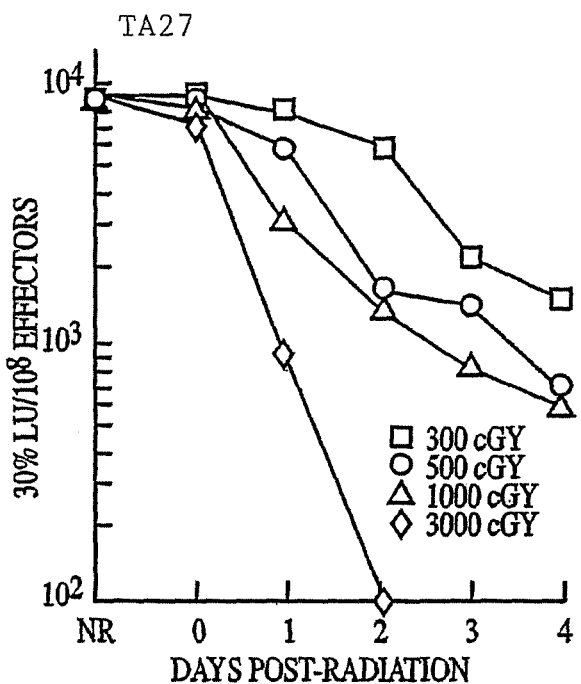
Figure 6D:
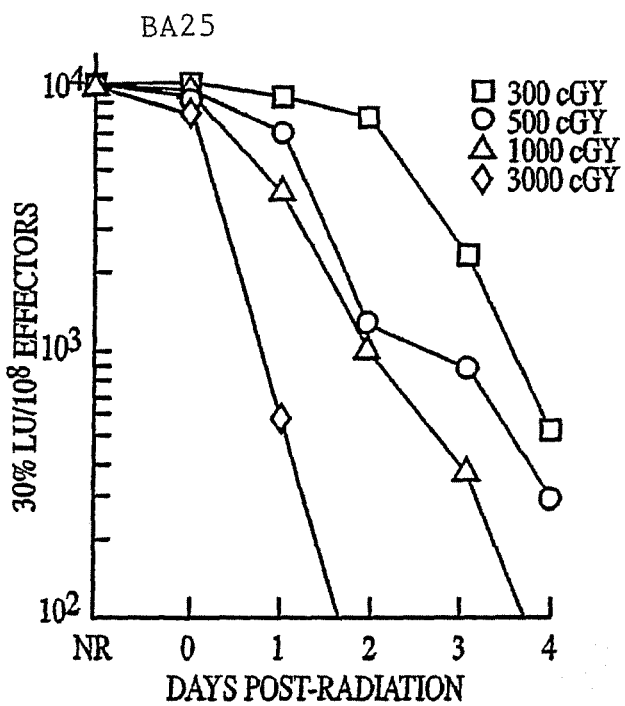

The viability of NK-92 cells, determined by trypan blue staining, and the recovery of the ability of the NK-92 cells to generate colonies after exposure to various radiation doses is shown in FIGS. 4 and 5, respectively. The NK-92 cells maintained substantial survival for 3 or 4 days after exposure to high doses of radiation (1000-3000 cGy). However, in vitro clonogenic NK-92 cells were significantly depleted after low doses of radiation and totally eliminated by doses above 300 cGy. FIG. 6 shows the cytotoxicity of NK-92 cells to K562, HL60 and 2 patient-derived leukemic samples after exposure to the different doses of radiation. Doses of 300, 500, and 1000 cGy allow for substantial cytolysis against leukemic cell lines and primary leukemias 1-2 days after radiation.

These experiments suggest that NK-92 cells, irradiated to an extent that renders them nonclonogenic, retain their cytolytic activity against a wide spectrum of target cells. They therefore may be used ex vivo in the purging of tumor cells as well as in the treatment of various cancers in vivo.

Example 9. Cytolysis of Human Primary Leukemic Cells by NK-92 a. Patient-Derived Leukemic Samples.

Samples were obtained, with informed consent, during routine diagnostic blood studies or bone marrow (BM) aspirates from patients with newly diagnosed or relapsed leukemias. 9 acute myeloid leukemia (AML) cases, 11 chronic myeloid leukemia (CML) cases (6 chronic phase, 1 accelerated phase and 4 blast crisis), 14 B-lineage-acute lymphoblastic leukemia (ALL) cases (13 pre-B-ALLs and 1 B-ALL) and 6 T-ALL cases, were studied (see Table 5). Blast-enriched mononuclear cells were isolated by Ficoll Hypaque (Pharmacia, Piscataway, N.J.) density gradient separation and washed in RPMI 1640 medium.

b. Effector Cells.

NK-92 cells were cultured and maintained in a-MEM medium supplemented with 12.5% FCS, 12.5% horse serum and rhIL-2 (500 U/mL Chiron, Emeryville, Calif.). TALL-104 cells (a MHC-unrestricted human cytotoxic T cell clone, generously provided by Drs. D. Santoli and A. Cesano, The Wistar Institute, Philadelphia) were maintained in Iscove's modified Dulbecco's medium supplemented with 10% FCS and rhIL-2 (100 U/mL) (Cesano et al., Blood, 87:393-403 (1996)). Another human NK cell clone, YT, was maintained in RPMI 1640 medium with 10% FCS and rhIL-2 (100 U/mL) (Yodoi et al., J. Immunol., 134:1623-1630 (1985)).

c. Cytotoxicity Assays.

The cytotoxic activity of non-irradiated NK-92 and responding T cells against leukemic targets was measured in a standard 4-hour chromium release assay (CRA). Some of the samples were also measured in an 18-hour CRA. A fixed number of $^{51}$Cr-labeled target cells (5×10$^3$/well) was tested for susceptibility to 4 effector cell concentrations. $^{51}$Cr release of target cells alone (spontaneous release, determined by placing target cells in 5% Triton) was always <25% of maximal $^{51}$Cr release. CRA data were expressed as specific lysis (%) at a given effector:target (E:T) ratio or were converted to lytic units (LU) defined as the number of effectors resulting in 30% lysis of target cells (Cesano et al., Cancer Immunol. Immunother., 40:139-151 (1995)). The degree of sensitivity of patient-derived leukemic cell targets to each effector was defined as insensitive (−/+: <10/10-19% lysis), sensitive (++/+++/++++: 20-29/30-39/40-49% lysis) and highly sensitive (+++++/++++++: 50-59/>60% lysis) at an E:T ratio of 9:1.

d. Results: Cytolysis of Human Primary Leukemic Cells by NK-92 Cells.

The sensitivity of patient-derived leukemic cells to the cytotoxic effect of NK-92 cells is summarized in column 4 of Table 5. Of the 40 patient-derived leukemic samples shown in Table 5, 26 (65%) were sensitive or highly sensitive to NK-92 mediated in vitro cytotoxicity. Six of the samples that were insensitive to the NK-92 cells in the standard 4 hr CRA (sole or first entries), became sensitive after 18 hours incubation (second entries, enclosed in parentheses). Leukemia blasts derived from 6 out of 9 (67%) AML, 6 of 6 (100%) T-ALL and 6 of 14 (43%) B-lineage-ALL were either sensitive or highly sensitive to the NK-92 mediated lysis. 7 of 8 acute leukemia samples which demonstrated high sensitivity to the cytotoxic effect of NK-92 cells were derived from relapsed patients and 1 was from a newly diagnosed patient. Out of 11 CML samples, 8 (73%)

were sensitive (5 in chronic phase) or highly sensitive (2 in blast crisis; 1 in accelerated phase) to the NK-92 mediated cytolysis (Table 5).

In comparison, the last two columns in Table 5 present results obtained with cell lines known in the field to have cytolytic activity against tumor cells, namely, TALL-104 cells and YT cells. Only 16 out of the 37 leukemic samples tested (43%) were sensitive (4 AMLs, 5 B-lineage ALLs and 3 CMLs) or highly sensitive (1 AML, 1 B-lineage-ALL and 2 CMLs) to the MHC unrestricted cytotoxic T cell clone TALL-104 mediated cytolysis. Leukemias sensitive to the TALL-104 cells were not consistently sensitive to NK-92 cells, and cells that were lysed by NK-92 cells were not always lysed by TALL-104 cells. In addition, the cytolytic activity of TALL-104 cells was usually detected only after 18 hours of incubation (second entries, enclosed in parentheses). Only four of 16 (25%) of the target samples that were lysed at 18 hours were also lysed in the standard 4 hr CRA. The remaining 12 (75%) responded only after the 18 hour incubation, with the response being generally lower than that observed with the NK-92 cells of the invention. Without wishing to be bound by theory, these observations may be due to the possibility that 1) different target structures are recognized by TALL-104 vs NK-92 cells, or 2) a different pathway may be involved in the NK-92 and in the TALL-104 cell mediated cytolysis.

The majority of leukemic samples treated with YT cells, the other NK-like clone tested, were found to be resistant, with the exception of 2 samples (a CML in blast crisis and a T-ALL) (see Table 5).

In conclusion, the NK-92 cells of the invention are surprisingly and significantly more effective in lysing patient-derived tumor cells, and exert their effect in a shorter time, than do the cells from two cytolytic cell lines known in the field.

TABLE 5

Cytotoxicity of NK-92, T-ALL 104 and YT Clone to Patient-Derived Leukemic Cells[a]

| Patient | Disease Status | Blast (%) in Sample | NK-92 | TALL-104 | YT |
|---|---|---|---|---|---|
| AML | | | | | |
| 1 M4☐ | Relapse | PB (66%) | ++++++ | +++++ | - |
| 2 (M1) | Relapse | PB (50%) | +++++ | - | - |
| 3 (M3) | Relapse | PB (50%) | +++ (++++) | + (++++) | - (-) |
| 4 (M4) | Refractory | PB (90%) | ++ (++) | - (+) | - (-) |
| 5 (M2) | New | BM (90%) | +++ (+++) | + (+++) | ND |
| 6 (M4) | New | BM (97%) | - | - | - |
| 7 (M4) | New | PB (39%) | - (-) | - (++) | - (-) |
| 8 (M3) | New | PB (55%) | - (++) | - (+++) | + (-) |
| 9 (M3) | New | BM (32%) | - | - | - |
| T-ALL | | | | | |
| 1 | Relapse | BM (98%) | ++++++ | - | - |
| 2 | Relapse | PB (85%) | ++++++ | - (-) | +++ (+++) |
| 3 | Relapse | PB (77%) | ++++++ | - (+) | - (-) |
| 4 | Relapse | PB (60%) | +++++ | - (-) | + (-) |
| 5 | New | BM (40%) | +++ | - | - |
| 6 | New | BM (66%) | +++ | - | - |
| B-Lineage-ALL | | | | | |
| 1● | Relapse | BM (78%) | +++++ | ++++ | - |
| 2 | New | BM (30%) | ++++ | ND | ND |
| 3 | Relapse | BM (75%) | +++ (++++) | + (++++) | ++ (++) |
| 4 | New | BM (97%) | ++ (+++) | + (+++) | - (-) |
| 5 | Relapse | BM (60%) | + (+) | - (+) | - (-) |
| 6 | Relapse | BM (80%) | - | ND | ND |
| 7 | Relapse | PB (80%) | - | - (-) | - |
| 8 | New | BM (68%) | - | - | - |
| 9 | New | BM (33%) | - | - (+) | - |
| 10 | Relapse | BM (87%) | - | - (++) | - |
| 11 | Relapse | BM (75%) | - (+++) | - (++++) | - |
| 12 | New | BM (30%) | - | - | ND |
| 13 | New | PB (90%) | - (+++) | - (+++) | ND |
| 14 | New | BM (81%) | - | - | ND |
| CML | | | | | |
| 1 | BC | PB (45%) | ++++++ | +++++ | +++ |
| 2 | AC | PB (22%) | ++++++ | ++ | - |
| 3 | BC | PB (93%) | +++++ | ++ | - |
| 4 | CP | PB (15%)D | ++++ | + | - |
| 5 | CP | PB (8%)D | ++ (++++) | ND | ND |
| 6 | CP | BM (12%)D | + (+++) | + (+) | ND |
| 7 | CP | BM (10%)D | + (+++) | + (++++) | ND |
| 8 | BC | PB (60%) | + | - | - |
| 9 | BC | BM (48%) | + | - (-) | - |
| 10 | CP | PB (21%)D | + (++) | - (++++) | - (-) |
| 11 | CP | PB (11%)D | - | - (+++++) | - (-) |

Notes and Abbreviations. [a]) Columns show results of chromium release assays at E:T = 9:1 after 4 h without parentheses, and (results after 18 h enclosed in parentheses); New: newly diagnosed; ND: none done; o: FAB classification; D: blast and promyelocyte; BM: bone marrow; PB: peripheral blood; I: B-ALL; BC: blast crisis; AC: accelerated phase; CP: chronic phase.

Example 10. Cytotoxicity of NK-92 Towards Human Leukemic Cell Lines

The following human leukemic cell lines were cultured at 37° C. in 5% $CO_2$ in RPMI 1640 medium supplemented with 10% heat-inactivated fetal calf serum (FCS), L-glutamine and antibiotics: K562 (Chronic myeloid leukemia in blast crisis), HL60 (acute promyelocytic leukemia), KG1 (erythroleukemia), NALM6 (acute pre-B lymphoblastic leukemia), Raji (Burkitt's lymphoma), CEM/S (acute T lymphoblastic leukemic cell line sensitive to methotrexate (MTX), a commonly used antitumor drug) as well as CEM/T (methotrexate-resistant subline of CEM/S) (Mini, E. et al., Cancer Res. 45:325-330 (1985)).

NK-92 cells were highly cytotoxic to all the 8 leukemic cell lines tested in a 4 hr standard CRA (Table 6). The MTX-sensitive T-ALL cell line CEM/S as well as its MTX-transport resistant subline CEM/T displayed a similar sensitivity to the NK-92 cells. This suggests that tumors that are not responsive to MTX treatment could be treated by administering NK-92 cells of the instant invention. Table 6 surprisingly shows highly effective cytolytic activity for NK-92 against all the target cells tested. The results obtained at the low E:T ratio of 1:1 are especially noteworthy.

In contrast, the cytolytic cell lines TALL-104 and YT have little or virtually no cytolytic activity against many of these target cells under these conditions; when active, their activity is generally lower than that for NK-92 at E:T of 1:1. TALL-104 was cytotoxic to K562, NALM6 and HL60 cells, however, Raji cells exhibited only 22.2% lysis at 9:1 E:T ratio and KG1 cells, CEM/S as well as CEM/T were resistant. The YT clone did not exhibit significant cytotoxic activity. Activity was found only against K562 cells and Raji cells, which showed a 32% and 25% lysis at 9:1 E:T ratio, respectively.

As shown in Table 6, NK-92 cells of the present invention have a significantly wider range of action and higher activities than the known cytolytic cell lines TALL-104 and YT.

These activities are higher than any previously reported values in the field of tumor cytotherapy.

TABLE 6

Specific Lysis of Human Leukemia Cell Lines by Natural Killer Cell Clones NK-92, TALL-104, and YT.

| | Specific Lysis (%) | | | | | | | | |
|---|---|---|---|---|---|---|---|---|---|
| | NK92 | | | TALL-104 | | | YT | | |
| | Effector:Target Ratio | | | | | | | | |
| Target | 9:1 | 3:1 | 1:1 | 9:1 | 3:1 | 1:1 | 9:1 | 3:1 | 1:1 |
| K562 | 94.1 | 91.2 | 82.1 | 88.5 | 85.2 | 72.5 | 34.2 | 28.2 | 18.4 |
| HL60 | 87.9 | 75.3 | 79.6 | 43.0 | 16.0 | 6.9 | 2.1 | 1.1 | 1.5 |
| KG1 | 64.6 | 53.8 | 43.7 | 2.7 | 0.5 | 0 | 0.1 | 0 | 0 |
| NALM-6 | 72.6 | 56.8 | 52.4 | 67.8 | 55.6 | 33.3 | 1.0 | 0.5 | 0 |
| Raji | 86.0 | 75.4 | 70.0 | 22.2 | 10.2 | 0.3 | 25.1 | 18.0 | 14.2 |
| TALL-104 | 57.3 | 53.2 | 44.1 | - | - | - | 3.2 | 1.4 | 0.9 |
| CEM/S | 56.6 | 48.8 | 34.7 | 2.7 | 1.6 | 0.9 | 0.9 | 0.4 | 0.3 |
| CEM/T | 57.5 | 42.1 | 39.1 | 1.5 | 0.6 | 0.3 | 1.2 | 0.1 | 0.2 |

Example 11. Effect of NK-92 Cells on Normal Human Bone Marrow Hematopoietic Cells Heparinized bone marrow collected from normal donors was separated by Ficoll Hypaque density gradient isolation to produce the mononuclear cells. Enrichment of hematopoietic cells and depletion of T cells was achieved by soybean lectin agglutination (SLA) of mature marrow elements and removal of residual T cells by resetting with sheep red blood cells (Reisner et al., *Lancet*, 2:327-31 (1981)).

Figure 7:
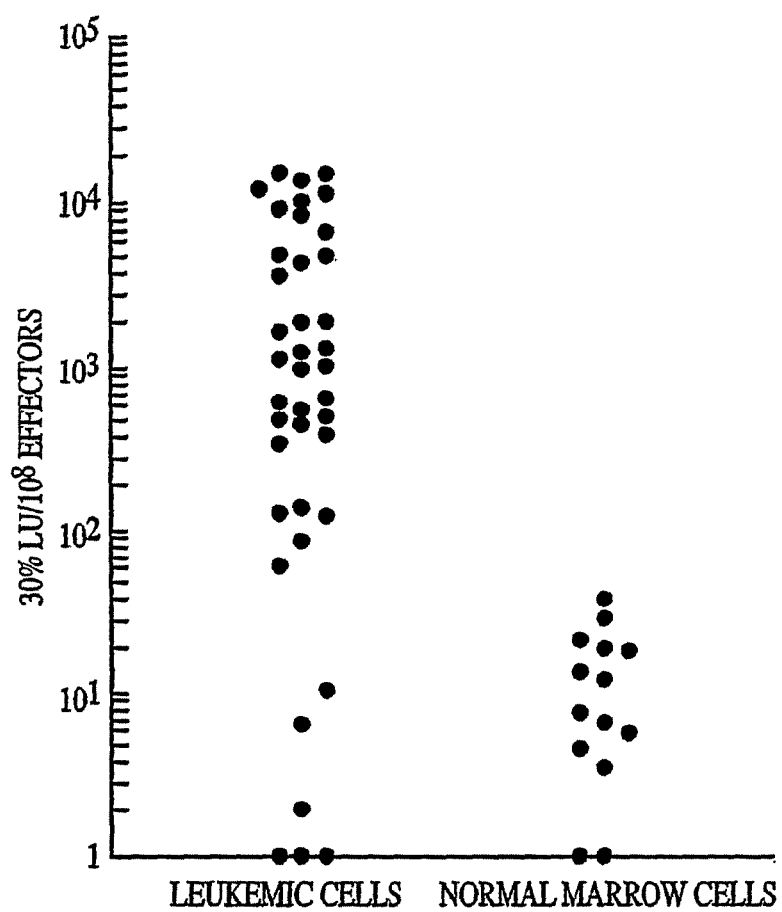
FIG. 7. Selective killing of patient-derived leukemic cells by NK-92 cells. $^{51}$Cr-labeled leukemic target cells derived from 40 patients [9 acute myeloid leukemia (AML) cases, 11 chronic myeloid leukemia (CML) cases, 14 B-lineage-acute lymphoblastic leukemia (ALL) cases and 6 T-ALL cases] and T cell depleted normal bone marrow cells from 14 normal donors were tested for susceptibility to cytolysis by NK-92 cells at four different E:T ratios. The results of a 4 hr chromium release assay are expressed as 30% lytic units/10$^8$ effector cells.
Figure 8A:
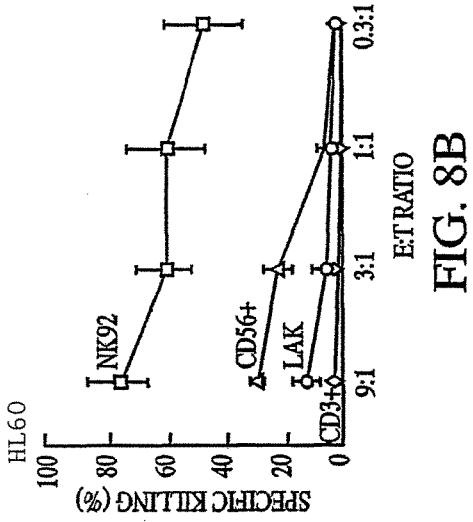
FIG. 8. In vitro (Panels A and B) and in vivo (Panels C and D) antileukemic efficacy of NK-92 cells against K562 and HL60 leukemias as compared to human LAK cells and other effectors. $^{51}$Cr labeled K562 (Panel A) and HL60 (Panel B) cells were tested for susceptibility to cytolysis by NK-92 cells in comparison with various known effector cells [LAK, NK (CD3$^-$ CD56$^+$), and T cells (CD3$^+$CD56$^-$)] at indicated E:T ratios in a 4 hr CRA assay. Results are means±SD of three separate tests for NK-92 cells, and two tests of different donor-derived effectors for LAK, CD56$^+$ and CD3$^+$ cells. SCID mice were inoculated subcutaneously with K562 cells (Panel C) or HL60 cells (Panel D) (5×10$^6$ cells per mouse) alone or in combination with NK-92, LAK, or NK cells at a 4:1 E:T ratio. As a measure of the tumor sizes, their surface areas were measured once a week post inoculation (n=5).
Figure 8B:
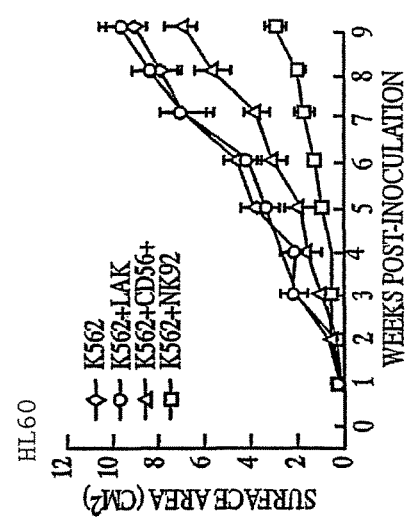
Figure 8C:
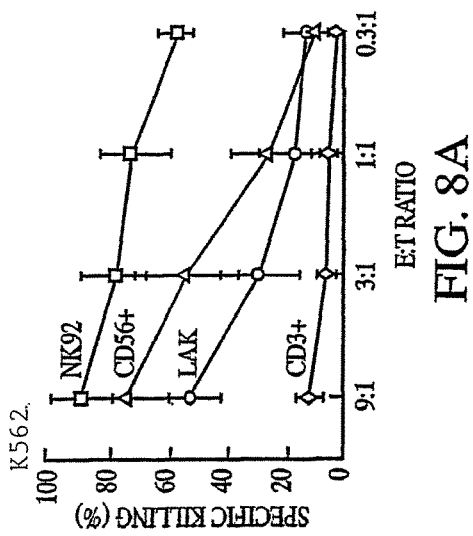
Figure 8D:
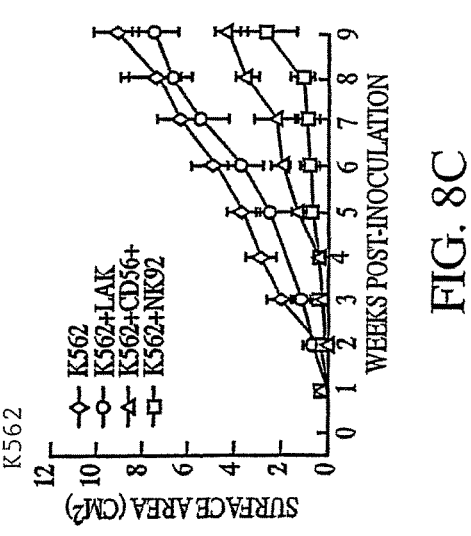

Hematopoietic cell enriched fractions of normal bone marrows from 14 normal donors were tested by standard CRA to determine their susceptibility to lysis by NK-92 cells. All of the normal bone marrow samples were insensitive to NK-92 mediated cytolysis (FIG. 7).

Example 12. In Vivo Leukemogenesis of NK-92 Cells in SCID Mice a. Experimental Animals.

Severe combined immunodeficient (SCID) mice (CB17 scid/scid and pfp/Rag-2) (6 to 8 weeks old; Taconic Farms, Germantown, N.Y.) were maintained in microisolator cages under sterile conditions with a specific pathogen-free environment. To determine the potential of NK-92 cells to induce leukemia in vivo, $2\times10^7$ viable NK-92 cells in 0.3 mL phosphate buffered saline (PBS) were administrated by either intraperitoneal (I.P.) or intravenous (I.V.) route every other day for 5 injections in each animal. For subcutaneous (S.C.) inoculations, $2\times10^7$ NK-92 cells were injected in the right flank of SCID mouse, as described previously (Yan et al., *Blood*, 88:3137-3146 (1996)). Thereafter, all the experimental animals were administered rhIL-2, $5\times10^4$ U every other day for 2 weeks by S.C. injection. Survival of the animals was followed for at least 6 months after inoculation.

b. Tissue Analysis.

From each group, 2 SCID mice were sacrificed at the end of observation and tissues from peripheral blood, bone marrow, spleen, liver, kidney, lung, and brain were collected for histopathological and/or fluorescence activated cell sorting (FACS) analysis. Tissue sections from sacrificed SCID mice were fixed in 10% neutral buffered formalin, dehydrated and embedded in paraffin, sectioned and stained according to standard histological techniques.

Viable cells recovered from various tissues were stained by fluorescein isothiocyanate-conjugated (FITC) or phycoerythrin-conjugated (PE) Mab, as described (Yan et al., (1996)). A FACS scan flow cytometer (Becton Dickinson) was used for analysis. Monoclonal antibodies (Mabs) directed against the respective human cell surface antigens were used for determination of their presence: CD2, CD3, CD5, CD7, HLA-DR, CD45, CD56 (Becton Dickinson). A fluorescein isothiocyanate (FITC)-conjugated rat anti-mouse Mab mCD45 (Boehringer-Mannheim, Indianapolis, Ind.) was used for characterization of murine leukocyte common antigen.

c. Leukemogenesis.

CB-17 scid/scid mice as well as pfp-Rag-2 mice were inoculated with NK-92 cells by I.V. (n=3, for each group), S.C. (n=2, each group) and I.P. (CB-17: n=8; pfp-Rag-2: n=3) injection. Survival of the animals was followed at least 6 months after inoculation. At the end of the six month period, all animals appeared healthy; there was no hepatosplenomegaly, lymphadenopathy or leukemic nodular growth, which would have indicated leukemia development. Leukemic cellular infiltration was not detected in the different tissues of the sacrificed animals by histopathology. No cells of human origin were detectable in the tissues by FACS analysis.

Example 13. Comparison of Antileukemic Effect of NK-92 Cells with LAK, NK and T Cells Against Human Leukemic Cell Lines To isolate the NK cell populations, a Ceprate$^R$ cell separation system based on avidin-biotin immunoaffinity (CeliPro, Bothel, Wash.) was used to purify a CD56+ cell fraction from cultured LAK cells. Briefly, the harvested cells were washed and resuspended in PBS with 1% bovine serum albumin (BSA). To each $1\text{-}2\times10^8$ cells/mL, 40 µL primary monoclonal antibody (mouse anti-human CD56) was added and the cells were incubated at 4° C. for 25 minutes. After incubation, the cells were washed and resuspended to a concentration of $1\times10^8$ cells per mL in PBS with 1% BSA. Then, to each one mL cell suspension, 20 µL biotin labeled rat antimouse IgG1 antibody was added and the cells were incubated again at 4° C. for 25 minutes. After incubation, the cells were washed and resuspended at a concentration of $1\times10^8$ cells per mL in PBS with 5% BSA and slowly passed through the avidin column. The CD56+ cells were captured; other cells, including the T cell fraction, were eliminated from the column. After washing the column, the adherent cells were then disassociated from the column by agitation and elimination. After separation, the NK cell-enriched populations contained >85% CD56+CD3− NK cells. The majority of the other cells in the fraction (>95%) were CD3+CD56− T cells.

To generate leukemia-reactive allocytotoxic T lymphocytes (CTLs), peripheral blood mononuclear cells (PBMC) isolated from normal donors were cultured with irradiated leukemic stimulating target cells and irradiated autologous PBMC as feeder cells. Cultures were started in 60 well plates at 1000 responder cells per well in RPMI 1640 medium containing 15% human serum and rhIL-2 100 U/mL at 37° C., 5% $CO_2$. The ratios of stimulator cells and feeder cells to responder cells were 5:1 and 10:1, respectively. After 10-12 days culture, CTLs were harvested from growth-positive wells and specific lysis toward leukemic target cells and K562 cells was quantitated by $^{51}$Cr-release assay. The CTLs were continuously cultured and fed with stimulator and feeder cells in flasks. After 2-3 weeks culture, the monoclonal antibody OKT3 (Ortho Biotech, Raritan, N.J.) was added to the culture for rapid expansion of the CTL lines.

The antileukemic effects of NK-92 cells, human LAK cells, NK cells (CD56+CD3−; CD56+ in FIG. 8), and T cells (CD3+CD56−; CD3+ in FIG. 8) were assessed by measuring in vitro cytolytic activity in standard CRA (FIG. 8, Panels A and B), and by measuring inhibition of leukemic cell xenograft growth in vivo (FIG. 8, Panels C and D) when the effector cells and targets were co-inoculated subcutaneously into SCID mice. In order to evaluate the inhibition of growth in vivo, the area of the subcutaneous growths of leukemic nodules as a measure of their size was determined once a week after inoculation, and survival of the animals was also followed. NK-92 cells displayed the highest in vitro cytotoxicity against K562 (FIG. 8, Panel A) and HL60 (FIG. 8, Panel B) of the cells tested, with a mean specific lysis of 89% and 78%, respectively. This was superior to the killing mediated by human LAK (52% and 11%, respectively), NK (72% and 28%, respectively) and T cells (12% and 1.2%, respectively).

Correspondingly, the NK-92 cells demonstrated more effective in vivo inhibition of the growth of K562 (FIG. 8, Panel C) and HL60 (FIG. 8, Panel D) leukemic cells xenografts than did the human LAK and NK cells. The results shown in FIG. 8 indicate that the NK-92 cells of the present invention have cytolytic activity in vitro and tumor-inhibiting activity in vivo that is superior to those activities manifested by the known preparations of cytolytic cells normally present in humans. These activities are therefore unexpected by a worker in the field of tumor cytotherapy.

Example 14. Comparison of Antileukemic Effect of NK-92 Cells with Allogeneic Leukemic-Reactive CTL Cells To examine the in vivo effects of NK-92 cells and other effector cells on the growth of human leukemia xenografts, $5 \times 10^6$ leukemic target cells alone or mixed with $2 \times 10^7$ NK-92 or other effector cells (E:T ratio=4:1) were injected S.C. into SCID mice. The TALL-104 effector cells were irradiated with 3000 cGy before inoculation to prevent leukemogenesis in SCID mice. RhIL-2 was administered to the mice, as in Example 13. The Log-rank test and Wilcoxon test were used for the comparison of the survival of leukemia bearing SCID mice.

Figure 9A:
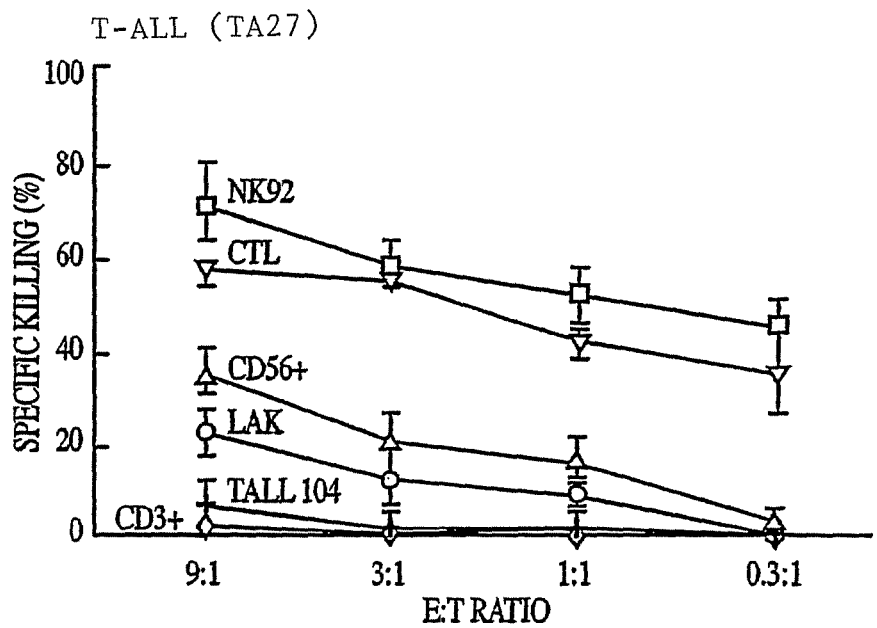
FIG. 9. Antileukemic effect of NK-92 cells, allogeneic cytotoxic T lymphocyte (CTL) cells and other effector cells against a patient-derived acute T lymphoblastic leukemia (T-ALL) determined in vitro and in vivo. Panel A: In vitro specific killing of T-ALL (TA27) target cells by NK-92, CTL, and other effector cells, was determined by a 4 hr $^{51}$Cr-release assay using the indicated E:T ratios. Results are means±SD of two or three separate tests. Panel B: SCID mice were inoculated subcutaneously with TA27 cells (5×10$^6$ each mouse) alone or co-inoculated with NK-92, CTL or other effector cells at a 4:1 E:T ratio. Recombinant human IL-2 (rhIL-2) was administered to the mice intraperitoneally for two weeks at the dose of 5×10$^4$ U every other day. Leukemic tumor areas were measured once a week post inoculation (n=5).
Figure 9B:
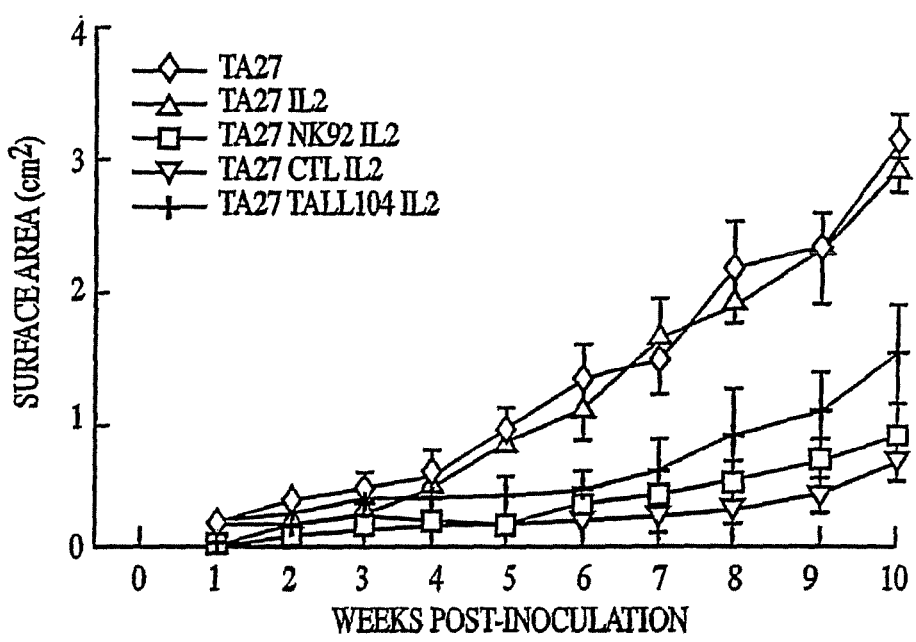
Figure 10:
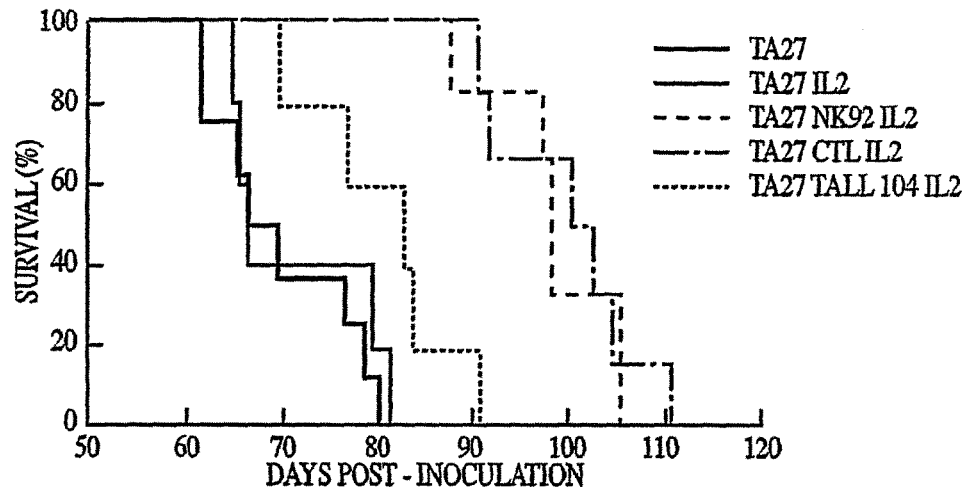
FIG. 10. Survival of SCID mice bearing T-ALL (TA27) leukemia co-inoculated with NK-92 cells as compared with co-inoculation with allogenic CTL or irradiated TALL-104 cells.

The antileukemia effect of NK-92 cells was evaluated using allogeneic leukemia-reactive CTL cells (derived from a patient with T-ALL (TA27)). Both NK-92 and CTL cells activated by exposure to TA27 displayed a significantly higher specific cytolysis (70% and 58% at 9:1 E:T ratio, respectively) than the other effectors (LAK cells: 22%; NK cells (designated CD56+ in FIG. 9): 38%; TALL-104: 8%; and T cells (CD3+ in FIG. 9): 1.5% specific lysis) against the TA27 leukemic cells (FIG. 9, Panel A). Correspondingly, the subcutaneous growth of TA27 leukemic cells was inhibited by co-injection of either NK-92 cells or anti-TA27-CTL cells (FIG. 9, Panel B). The survival of those animals which were co-inoculated with TA27 leukemic cells plus NK-92 or with anti-TA27-CTL cells was significantly prolonged beyond that of the animals bearing TA27 leukemia alone (NK-92 cells: p=0.001; TA27-CTL cells: p=0.002; see FIG. 10). In contrast the TALL-104 cells did not show significant in vitro killing against TA27 leukemic cells by CRA (FIG. 9, Panel A). However, moderate inhibition of the leukemic tumor growth in vivo (FIG. 9, Panel B), coupled with a statistically insignificant (p>0.05) increase in survival, was observed in the animals co-inoculated with TA27 leukemic cells and irradiated TALL-104 cells (FIG. 10).

Example 15. Antileukemia Effect of NK-92 Cells in Human Leukemia Xenograft SCID Mice Model For study of the in vivo tumoricidal capacity of NK-92 cells, leukemic cells derived from a T-ALL patient (TA27), an AML patient (MA26), and a pre-B-ALL patient (BA31) were adoptively grown and expanded in SCID mice by S.C. inoculation. Leukemic cells recovered from the leukemic nodules in the mice (first passage) were used in these experiments. The SCID mice in each group were inoculated I.P. with $5 \times 10^6$ leukemic cells from the first passage in 0.2 mL PBS, and 24 hours later $2 \times 10^7$ NK-92 cells in 0.4 mL PBS were administered by I.P. injection. The animals received either 1 dose or a series of 5 doses of NK-92 cells which were administered on days 1, 3, 5, 7, and 9, with and without rhIL-2, as indicated in the Figures.

Figure 11:
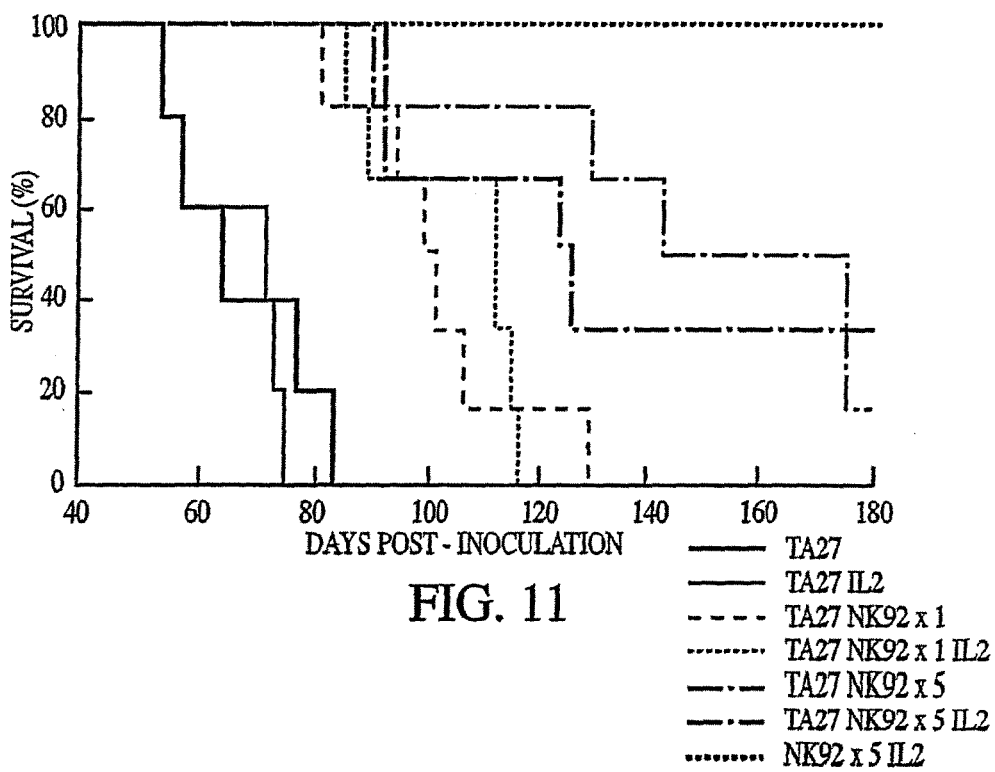
FIG. 11. Survival of SCID mice bearing T-ALL (TA27) after treatment with NK-92 cells. Mice received $5 \times 10^6$ TA27 cells intraperitoneally (I.P.). NK-92 cells ($2 \times 10^7$) were injected I.P. once, or 5 times (on days 1, 3, 5, 7 and 9), with or without the addition of rhIL-2 every other day for two weeks.

All the human leukemias grew aggressively in SCID mice. Leukemic cells derived from a patient (TA27) with T-ALL and a patient (MA26) with AML M4 leukemia were highly sensitive in vitro to the NK-92 cells (73% and 66% specific killing at 9:1 E:T ratio determined by CRA, respectively), whereas cells from a patient with pre-B-ALL (BA31) were insensitive to the NK-92 cells (4% specific killing at 9:1 E:T ratio assessed by CRA). FIG. 11 shows that the survival of mice bearing TA27 leukemia was significantly prolonged by the administration of NK-92 cells. The median survival time (MST) of the animals with no treatment or rhIL-2 alone was 72 days (n=5) and 63 days (n=5) (p>0.05), respectively. All these animals died of leukemia. Treatment with NK-92 cells (alone or with rhIL-2) increased the MST to 102 days (n=6) and 114 days (n=6), respectively, for the 1 dose injection schedule ($2 \times 10^7$ NK-92 cells, day 1). The MST increased to 160 days (n=6) and 129 days (n=6), respectively, with 5 doses NK-92 with or without rhIL-2 injection (FIG. 11). Three animals that received 5 doses of NK-92 cell injections with or without rhIL-2 administration survived without any signs of leukemia development 6 months after inoculation. There was no significant difference in survival between the mice receiving treatments with or without rhIL-2 administration, whether in the group receiving 1 dose of NK-92 cells (p=0.75), or the in the group receiving 5 doses (p=0.45). Compared to the group receiving 1 dose of NK-92 cells, with or without rhIL-2 treatment, survival was significantly extended in animals that received 5 doses of NK-92 cells without rhIL-2 treatment (p=0.009 and p=0.009, respectively).

Figure 12:
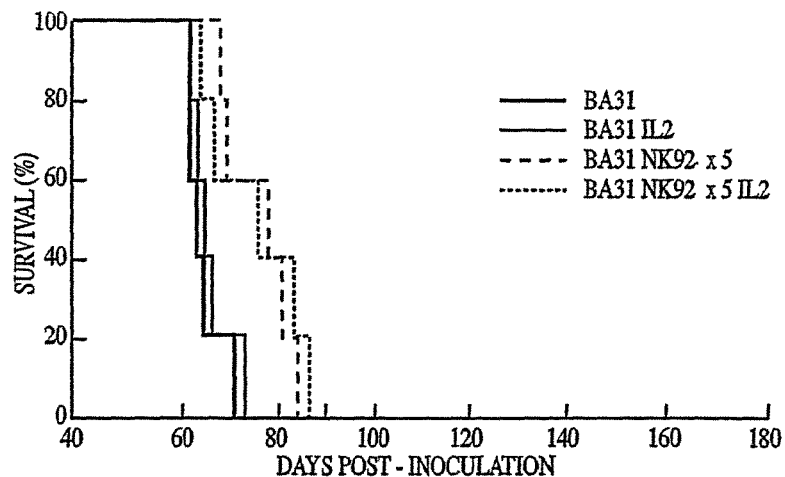
FIG. 12. Survival of SCID mice bearing pre-B-ALL (BA31) after treatment with NK-92 cells. Mice received $5 \times 10^6$ BA31 cells I.P. NK-92 ($2 \times 10^7$) cells were injected I.P. for a total of 5 doses, on days 1, 3, 5, 7 and 9.

In SCID mice inoculated with human pre-B-ALL (BA31) leukemia, with or without rhIL-2 treatment, the MST were 63 days (n=5) and 64 days (n=5), respectively (see FIG. 12). For the animals that received 5 doses of $2 \times 10^7$ NK-92 cells, with or without rhIL-2 administration, the MST was increased to 79 days (n=5) and 76 days (n=5), respectively. These survival times were not significantly different from those for the animals that were not treated by NK-92 cells (p>0.05).

In animals bearing human AML (MA26), MST was 97 days (n=6) (see FIG. 13). The MST was extended to 173 days among the animals that received 5 doses of $2 \times 10^7$ NK-92 cells (p<0.01)(n=6). Three of the 6 animals that received NK-92 cells remained alive 6 months after leukemia inoculation. Two of these appeared healthy without any signs of leukemia development. One mouse had an enlarged abdomen indicating residual leukemia. The 6 animals that received NK-92 cells plus rhIL-2 treatment were all alive 6 months after leukemia inoculation without any signs suggestive of leukemia development.

The results presented in FIGS. 11-13 show that in vivo treatment of leukemic tumors can result in enhanced longevity of the subject mice. The extent of the prolongation of life, and of the improvement in the health of the animals, is dependent on the particular leukemic tumor involved, and ranges from modest or insignificant (FIG. 12) to very dramatic (FIG. 13). Based on these results, it is concluded that treatment of tumors in vivo by administering NK-92 cells, depending on the tumor in question, can be surprisingly effective.

Example 16. Preparation of Modified NK-92 Cell Lines Secreting IL-2

In order to generate NK-92 cells that constitutively secrete IL-2, two plasmids encoding human IL-2 were employed.

a. Methods.

DNA Clones: The MFG-hIL-2 vector (FIG. 14) was generously provided by Dr. Craig Jordan (formerly of Somatix Corp., Alameda, Calif.). The pCEP4-LTR-hIL-2 vector (FIG. 15) was created by excising the Hin DIII-Barm HI fragment from the MFG-hIL-2 vector, containing the 5' LTR and hIL-2 gene, and inserting it into the complementary sites of the pCEP4 episomal vector backbone (InVitrogen, Carlsbad, Calif.).

Particle-Mediated Gene Transfer: NK cells were transduced by particle-mediated gene transfer using the Biolistic PDS-1000/He Particle Delivery System (BioRad Laboratories, Hercules, Calif.). Cells were transduced according to the manufacturer's instructions. Briefly, 1.0 or 1.6 μm gold particles were coated with 5 μg of DNA using calcium chloride spermidine, and ethanol. NK-92 cells were prepared for bombardment by adherence to poly-L-lysine (Sigma, St. Louis, Mo.) coated 35 mm tissue culture plates. Cells were bombarded in an evacuated chamber (vacuum of 20 inches mercury) and DNA-coated particles were accelerated by a 1,100 psi helium pulse. Cells were returned to IL-2 supplemented Myelocult media immediately following bombardment and allowed to recover for 24 hours prior to transfer to IL-2-free media. Media was changed periodically. Cells were selected for IL-2-independent growth. Preliminary experiments showed heat transfer efficiencies of 5-15% were obtained under the conditions used.

PCR and Southern Blot Analysis: The transfection of the NK-92 cells was confirmed by polymerase chain reaction (PCR) analysis of DNA isolated from both the parental and transfected NK-92 cell lines for the presence of genomic and cDNA forms of the human IL-2 gene. DNA was isolated using DNAzol (Gibco Life Technologies Inc., Burlington, ON). Briefly, cells were lysed in DNAzol and DNA was precipitated with ethanol at room temperature. DNA pellets were collected, washed in 95% ethanol and briefly air dried. DNA was resuspended in 8 mM NaOH at 62° C. and the solution was neutralized with HEPES buffer. DNA was quantitated by absorbance at 260 nm. Primers flanking exon 1 of the human IL-2 gene (forward: 5'-CAA CTC CTG TCT TGC ATT GC-3' (SEQ ID NO:1) and reverse: 5'-GCA TCC TGG TGA GTT TGG G-3' (SEQ ID NO:2), Gibco Lift Technologies Inc., Burlington, ON) were used to amplify the DNA (30 cycles, 1 min 95° C., 2 min 50° C. and 2 min 72° C.). PCR products were resolved on a 2% agarose gel. For Southern blot analysis, DNA was transferred to Hybond+ nylon membrane (Amersham Life Sciences, Arlington Heights, Ill.) by capillary transfer in 10×SSC (1.5M NaCl, 1.5M NaCitrate) and fixed by UV cross-linking (StrataLinker Stratagene, La Jolla, Calif.). The blot was hybridized with a $^{32}P$ radiolabeled human IL-2 probe for 8-12 hours, washed and visualized by autoradiography at −70° C. with Kodak X-Omat XAR film.

Northern Blot Analysis: Cytokine and chemokine gene expression was analyzed by Northern blot analysis. RNA was extracted from parental and transfected NK-92 cell lines using Trizol reagent (Gibco Life Technologies Inc., Burlington, ON) according to the manufacturer's instructions. Briefly, cells were lysed in Trizol and the lysate extracted with chloroform. The aqueous phase was then precipitated with isopropanol. The RNA pellet was collected, briefly air-dried and then resuspended in DEPC-treated water (diethyl-pyrocarbonate; Sigma Chemical Co., St. Louis, Mo.). RNA was quantitated by determining $OD_D$. Fifteen micrograms of RNA was resolved on a 1% formaldehyde agarose gel in 1% MOPS (3-[N-Morpholino]propanesulfonic acid, Sigma, St. Louis, Mo.) and blotted as described previously for Southern blot analysis. The blot was hybridized with $^{32}P$ radiolabeled probes for human IL-2 and TNF-α.

DNA probes for Northern and Southern blot analysis were radiolabeled by random primer extension. DNA probes for human IL-2 and TNF-α were purified by digestion with appropriate restriction endonucleases and agarose electrophoresis. The DNA was excised from the gel and purified by centrifugation through a Spin-X tube filter (Corning Costar, Cambridge, Mass.), phenol:chloroform extraction and ethanol precipitation. DNA probe was labeled with a $^{32}P$-dCTP (Sp. Ac. 3000 Ci/mmol; ICN, Montreal, PQ).

Cytokine Determination: IL-2 production by NK-92 cell lines was determined by ELISA. Aliquots of $1 \times 10^6$ of the parental or transfected NK-92 cells were cultured in 8 ml of IL-2 free Myelocult media for 1, 2, and 3 days. Supernatants were collected from at −20° C. until all samples were collected. Samples were thawed and assayed for IL-2 levels by ELISA according to the manufacturers' instructions (Quantikine; R&D Systems, Minneapolis, Minn.). The ELISA is a horseradish peroxidase/tetramethylbenzidine based colorimetric assay and the ELISA microtiter plates were read at 450 nm (with a 540 nm correction) in a microplate reader (Model EK309, Bio-Tek Instruments Inc., Winooski, Vt.).

Irradiation of NK-92 Cells: To determine the sensitivity of both parental and transfected NK-92 cells to irradiation, cells were irradiated using a Cis BioInternational 437c cesium source (Cis-US, Bedford, Mass.). Cells were collected, washed and resuspended in medium and irradiated in 15 or 50 ml conical centrifuge tubes (Becton Dickinson, Franklin Lakes, N.J.). Following irradiation, cells were washed and resuspended in Myelocult with (for parental NK-92) or without (for transfected cells) IL-2. Cells were cultured for 24, 48 and 72 hours and assayed for viability by trypan blue exclusion, for proliferation by $^3H$ thymidine incorporation and for cytotoxicity by $^{51}Cr$-release assay (as described above).

b. Plasmid MFG-hIL-2.

For NK cells transfected with the MFG-hIL-2 vector, 85-95% of cells died after 4-7 days following transfer to unsupplemented media. A small number of cells, however, remained viable. These were assumed to be cells that had been successfully transfected. However, even with these cells, no viable cells were detectable after two to three weeks. This was expected as the MFG-hIL-2 vector construct did not contain the genetic elements required for replication and maintenance in eukaryotic cells such as a mammalian origin of replication. Therefore, as the transfected cells were maintained in culture and began to replicate, the vector construct would have been lost from cells and the cells would have reverted to their IL-2-dependent phenotype. These cultures were nevertheless propagated for several weeks. Surprisingly, a small number of viable cells appeared in the cultures after approximately 4-5 weeks following initial transfer of the cells to IL-2-free media. These cells were capable of IL-2-independent growth upon subculturing to fresh media and appeared to be stably transfected, maintaining their IL-2 independent phenotype during prolonged culturing. Since the vector was unable to replicate, the appearance of stably transfected cells suggests that the vector had integrated into the genome of a transfected cell. Since this would be a very rare event, these transfected cells probably arose from one or a very small number of cells. IL-2-independent NK-92 cells arising from transfection with the MFG-hIL-2 were denoted as NK-92MI.

c. Plasmid pCEP4-LTR.hIL-2.

Initial observations for cells transfected with the episomal vector pCEP4-LTR.hIL-2 were identical to those seen with NK-92MI. The majority of the transfected cells died within 4-7 days following transfer to IL-2-free Myelocult media. However, unlike the NK-92MI cells, the remainder of the cells did not lose their IL-2-independent phenotype or vitality and die after the initial 2-3 week period. Instead, the cells that were initially IL-2-independent were immediately capable of long-term IL-2-independent growth and survival. This was expected since the pCEP-LTR.hIL-2 vector contains elements that enable it to be maintained in eukaryotic cells as an autonomously replicating genetic element. Therefore, any cell that was initially transfected should maintain its IL-2-independent phenotype for an indefinite length of time. Although cells harboring episomal vectors are not stably transferred by strict definition, these cells are under constant selection pressure in IL-2-free media in favor of cells maintaining the vector. Therefore, these cells are capable of long-term culturing: IL-2-independent NK-92 cells arising from transfection with the pCEP4-LTR.hIL-2 are denoted as NK-92CI.

To confirm that NK-92MI and NK-92CI had in fact been transfected with hIL-2 gene, PCR analysis was performed on the parental and transfected cell lines. Primers flanking exon 1 of the hIL-2 gene, which has 88 base pairs (bp), were used to amplify DNA isolated from NK-92, NK-92MI and NK-92C1 to assay for the presence of the genomic and cDNA forms. Agarose gel electrophoresis of the PCR products from the parental line revealed a single 263 bp fragment corresponding to the size expected for the DNA fragment amplified from the genomic IL-2 gene. However, analysis of both the NK-92MI and NK-92CI products revealed two bands, the 263 bp fragment corresponding to the genomic hIL-2 gene as well as a 175 bp fragment resulting from the amplification of the hIL-2 cDNA. To confirm the identity of these DNA fragments, Southern blot analysis with a radiolabeled probe specific for hIL-2 was performed. Both the 263 bp genomic fragment and the 175 bp cDNA fragment hybridized with the probe. These data indicate that both NK-92MI and NK-92CI had been successfully transfected and contained the cDNA for hIL-2.

d. Analysis of Gene Expression.

Expression of specific cytokines in the parental and transfected cell lines, they were analyzed by Northern blot analysis. RNA isolated from NK-92, NK-92MI, and NK-92CI cells was separated by electrophoresis, transferred to a nylon membrane and hybridized with probes for the cytokines hIL-2 and hTNF-α. Northern blot analysis of IL-2 revealed that IL-2 RNA was not detectable in the parental cell line. However, hIL-2 RNA was detected in both NK-92MI and NK-92CI. Two mRNA transcripts were detected in NK-92MI cells: a major RNA species of approximately 1.9 kDa and a less intense transcript at 2.4 kDa. In NK-92CI, a hIL-2 mRNA transcript of approximately 1.4 kDa was detected. A very faint band was also seen at 2.5 kDa. These data confirm that the transfected cells expressed IL-2 while the parental NK-92 cells did not. The significance of the multiple hIL-2 mRNA transcripts in the two transfectants is not clear, although it is possibly a consequence of the different vector constructs. Furthermore, in the case of NK-92MI, the integration of the hIL-2 gene into the genomic DNA may also have affected the RNA size.

TNF-α expression in the NK cells was also examined using this technique. It was seen that all three lines expressed the gene for this cytokine. A TNF-α probe hybridized to a 1.6 kDa band in RNA isolated from NK-92, NK-92MI and NK-92CI. These results indicate that although transfection of NK-92 cells with the IL-2 gene resulted in expression of the IL-2 in the transfectants, this did not influence the expression of another cytokine.

e. Secretion of hIL-2.

After confirming expression of the IL-2 gene by Northern blot analysis, cells were assayed for production and secretion of hIL-2 by ELISA. Aliquots of $10^6$ NK-92, NK-92MI and NK-92CI cells were plated in 8 mL aliquots and cultured in Myelocult in the absence of IL-2. Supernatants were collected after 24, 48 and 72 hours for IL-2 analysis by ELISA. Background levels of IL-2 were detected in the supernatant of NK-92 cells at all three time points (2-3 pg/mL). Elevated IL-2 levels were detected in both NK-92MI and NK-92CI supernatants (Table 7). NK-92MI produced much higher levels of IL-2 in comparison to NK-92CI, with levels ranging from 60× higher after 24 hours (9.3 pg/mL vs 549.3 pg/mL) to about 80× higher after 48 hours (15.7 pg/mL vs 1,260.3 pg/mL) and 72 hours (27.2 pg/L vs 2,248.3 pg/mL).

TABLE 7

Synthesis of Human IL-2 by NK-92, NK-92MI, and NK-92CI

| | | IL-2 (pg/ml) in Experiment | | | |
|---|---|---|---|---|---|
| | | #1 | #2 | #3 | Ave ± S.D. |
| NK-92 | Day 1 | 0 | 7 | 1 | 2.7 ± 3.8 |
| | Day 2 | 0 | 4 | 1 | 1.7 ± 2.1 |
| | Day 3 | 0 | 3 | 3 | 2.0 ± 1.7 |
| NK-92MI | Day 1 | 517 | 568 | 545 | 549.3 ± 34.7 |
| | Day 2 | 977 | 1462 | 1342 | 1260.3 ± 252.6 |
| | Day 3 | 1872 | 2610 | 2263 | 1148.3 ± 369.2 |
| NK-92CI | Day 1 | 7 | 13 | 8 | 9.3 ± 3.2 |
| | Day 2 | 14 | 16 | 17 | 15.7 ± 1.5 |
| | Day 3 | 52 | 18 | 13 | 27.7 ± 21.2 | f. Comparison of Cell Surface Antigens in NK-92, NK-92MI and NK-92CI.

To compare the IL-2-independent transfectants with the parental cells, NK-92MI and NK-92CI were analyzed for CD2, CD3, CD4, CD8, CD10, CD16, CD28, CD56, ICAM-1, ICAM-2, ICAM-3 and LFA-1 expression by fluorescent activated cell sorting (FACS) analysis. The transfected cells revealed a pattern of expression identical to that seen on the untransfected parental cell line with the exception of the IL-2 receptor. FACS analysis of CD25 (the IL-2 receptor α-chain) on NK-92 cells indicated that the receptor was expressed on the surface of NK-92 cells and that its expression is down-regulated in response to IL-2. This confirmed similar findings obtained in earlier work (Gong et al., 1994). Therefore, NK-92 cells in unsupplemented media had relatively high levels of CD25 on their surface while cells in media supplemented with as low as 100 U/mL had low levels of CD25 cell surface expression.

CD25 expression in the high IL-2-producing transfectant NK-92MI was decreased both in unsupplemented media and in media supplemented with 100 U/mL or 1000 U/mL of IL-2. These results are consistent with those seen with the parental cells. Since the levels of endogenously produced IL-2 in NK-92MI were high, down-regulation of IL-2 receptor levels is expected even in the absence of exogenously administered IL-2.

Culture of NK-92CI in media supplemented with 100 U/mL and 1000 U/mL IL-2 resulted in CD25 upregulation and increased cell surface expression. However, the results for NK-92CI in unsupplemented media are not as clear. Two distinct populations appear, a population expressing very low CD25 levels, similar to NK-92MI, and a population expressing high levels, similar to the NK-92 parental cells. This suggests that NK-92CI consists of a polyclonal population consisting of high and low IL-2 expressing cells rather than a uniform population of cells expressing an intermediate to low level of IL-2. Therefore, when cultured in IL-2-free media, the cells expressing high levels of IL-2 would have low surface levels of CD25 while low IL-2 expressing cells would have high CD25 levels on their surface.

Example 17. Cytotoxicity of NK-92 Transfected to Produce IL-2

To evaluate the cytotoxicity of these transfected cells, a standard 4 hour $^{51}$Cr-release assay was performed to compare the toxicity of the parental cells to NK-92MI and NK-92CI to the standard test target cells K562 and Raji. The cytotoxicity of NK-92MI and NK-92CI was comparable to that seen with the parent cells (FIG. 16). The transfected cell lines show cytotoxic activities against K562 and Raji that are very similar to that of the parental cells. Cytotoxicity of NK-92 against K562 ranged from 82 to 67% while NK-92MI and NK-92CI had cytotoxicity ranges of 77 to 62% and 82 to 62%, respectively. For Raji cells, NK-92 had cytotoxicity of 81 to 47%, NK-92MI had cytotoxicity of 75 to 65% and NK-92CI had cytotoxicity of 82 to 52%.

Example 18. Effect of Transfected NK-92 Cells on Hematopoietic Progenitor Cells One potential clinical application of the NK-92, NK-92MI and NK-92CI cells is as an ex vivo purging agent for autologous grafts. In order for the NK cells to be suitable for such a purpose, they must be able to purge the malignant cells without killing the hematopoietic progenitor cells in the graft or influencing their hematopoietic potential. In order to assay this, a colony-forming cell assay (CFC) was performed where the clonogenic output of PBMCs was examined following a 48 hour incubation with NK-92MI and NK-92CI at various E:T ratios. NK-92 was previously shown to have minimal effect on hematopoietic stem cells (Example 6). In this example, NK-92MI and NK-92CI also show little or no effect on clonogenic output. The number of total colonies following incubation with either NK-92MI or NK-92CI was very similar to control, although a slight decrease was seen with the highest effector:PBMC ratio of 1:1 (FIG. 17). Total clonogenic output from both NK-92MI and NK-92CI was approximately 80% of control under this condition. However, no consistent trend was seen in terms of clonogenic output with respect to the ratio of NK:PBMCs. In terms of specific colony types, there were no detectable differences in the number of output BFU-E colonies, which are the most numerous. Some effect was seen with both the CFU-GM and CFU-GEMM colonies. However, the absolute numbers of these colonies are very low, making any conclusions difficult since small variations in the number of colonies has a large effect on the calculation of clonogenic output. An influence on CFU-GM and CFU-GEMM is seen at higher ratios, but no consistent correlation between ratio and output was noted.

Example 19. Irradiation of the Transfected NK-92 Cells

To establish an effective irradiation dose to inhibit proliferation and maintain cytotoxicity, NK-92MI and NK-92CI cells were irradiated at 500, 1,000, 1,500 and 2,000 cGy and assayed for proliferation by the $^3$H thymidine incorporation assay (see Examples 7 and 8). Both NK-92MI and NK-92CI were more sensitive to irradiation than the parental NK-92 cell. Proliferation of NK-92MI and NK-92CI was found to be more strongly suppressed than NK-92 at all radiation doses tested (FIG. 18, Panel A). For NK-92MI and NK-92CI, proliferation was completely suppressed by a radiation dose between 500 and 1,000 cGy. The level of thymidine incorporation reached a plateau at approximately 20% of unirradiated control cells for NK-92CI and 10% for NK-92MI. For determination of viability, NK-92, NK-92MI and NK-92CI cells were irradiated at 250, 500, 1,000 and 2,000 cGy and trypan blue exclusion was determined 24, 48 and 72 hours following irradiation. It was found that greater percentages of both NK-92MI and NK-92CI were found to be killed by irradiation as compared to the parental cells at equivalent doses (FIG. 18, Panel B). Viability of NK-92 was higher than that of both transfectants at all dose rates tested.

The cytotoxicity of these cells following irradiation is shown in FIG. 19. Cells irradiated at 0, 1,000 and 2,000 cGy were tested after three days for cytotoxicity against K562 and Raji cells at effector:target ratios of 20:1, 10:1, 5:1 and 1:1. Cytotoxicity of NK-92 cells three days following irradiation at 1,000 cGy was determined to be approximately 10-30% K562 (FIG. 19, Panel A) and 30-50% and for Raji (FIG. 19, Panel B). Irradiation at 2,000 cGy resulted in cytotoxicity of 1-5% against K562 and 3-13% against Raji. In contrast, NK-92MI had only 0-5% and 0-1% cytotoxic activity against K562 and 0-1% and 0% against Raji three days after irradiation doses of 1,000 and 2,000 cGy, respectively. NK-92CI had only 1-4% cytotoxicity to K562 and 2-7% to Raji three days after irradiation at 1000 cGy and 0% to K562 and 0-2% after irradiation with 2000 cGy.

In the data reported here, IL-2 transfectants are seen to be more sensitive to irradiation than the parental strain. Proliferation and cytotoxicity of both NK-92MI and NK-92CI cells were suppressed at a lower radiation level than for the parental strains, and radiation-induced lethality was much greater in the IL-2-independent modified cells in NK-92 at equivalent radiation doses. The high IL-2-producing NK-92MI is more sensitive to radiation than the low IL-2 producing NK-9201 variant. As a result of the increased radiation sensitivity, a reduced level of irradiation would be sufficient to adequately control proliferation while minimizing lethality to the cells and inhibition of cytotoxicity. In routine experiments, the worker of ordinary skill would be able to repeat experiments such as those described in this example. By using lower radiation doses, in the range between 0 and 1000 cGy optimal doses can be determined that inhibit proliferation while maintaining viability and cytolytic activity in NK-92MI and NK-92C1.

Example 20. Transfection of NK-92 with a Gene for Thymidine Kinase

NK-92 cells are to be transfected with a vector bearing a gene for thymidine kinase (TK). The resulting TK-modified NK-92 cells are thereby rendered susceptible to the toxic effects of the guanosine analogs, gancyclovir, and acyclovir.

A vector suitable for transfecting a mammalian cell is to be constructed, such as a retroviral vector harboring a herpes simplex virus (HSV) TK gene, under the control of the HSV TK promoter, and containing its own polyA addition site. Transfection is to be carried out by a method known to those skilled in cell biology and mammalian molecular biology, such as by electroporation (Bio-Rad Gene Pulser™), or by lipofection (Feigner et al., *Proc. Natl. Acad. Sci. USA* 84:7413 (1987)). The transfected NK-92 cells so produced are susceptible to inactivation by administering gancyclovir or acyclovir.

Example 21. Mutation of NK-92 HLA Cell Surface Protein

NK-92 cells are to be obtained from the cell line described by Gong et al. (1994). The chromosome bearing the $\beta_2$-microglobulin gene is to be isolated, and the DNA contained within this chromosome is to be purified away from histones and other DNA-bound proteins. The gene fragment bearing $\beta_2$-microglobulin is to be excised with restriction nucleases, and site specific mutagenesis is to be conducted via an oligonucleotide cassette harboring the mutated nucleotide sequence. These procedures employ techniques commonly known in recombinant DNA technology, as set forth, for example, in "Current Protocols in Molecular Biology", Ausubel et al., John Wiley and Sons, New York 1987 (updated quarterly), and "Molecular Cloning: A Laboratory Manual", 2nd Ed., Sambrook, Fritsch and Maniatis, Cold Spring Harbor Laboratory, Cold Spring Harbor, N.Y., 1989, incorporated herein by reference. The mutated $\beta_2$-microglobulin is to be reincorporated into the cellular DNA, and reintroduced into the NK-92 cells. This preparation of cells will then express cell surface HLA molecules incorporating mutated $\beta_2$-microglobulin moieties, and will have lost the ability to bind T-cell receptors.

Example 22. NK-92 Cells Expressing Receptors for a Cancer Cell

The CTL of a patient suffering from a cancer are to be harvested by differential centrifugation on a density gradient. The CTL are to be immunoaffinity purified to contain predominantly the CTL targeting a receptor on the cancer cell from the patient. The DNA of the CTL population obtained is to be isolated, and the genes for the MHC class I receptor in the cancer-targeted CTL isolated by restriction nuclease cleavage. The genes so purified are to be amplified using the polymerase chain reaction, and the resulting amplified genes incorporated into a vector suitable for the constitutive expression of the genes in NK-92 cells. The vectors are to be transfected into NK-92 cells, and the modified NK-92 cells so obtained are to be selected using, for example, an antibiotic resistance marker incorporated into the vector. The cells so selected are to be cultured to increase their number. They may then be employed to target specifically the cancer cells in the patient, and treat the cancer occurring in the patient either ex vivo or in vivo.

Example 23. Use of NK-92 Cells to Kill HIV-Infected Cells

8E5 is a cell line harboring HIV that produces HIV virions. 8E5L is a corresponding cell line infected with HIV which does not produce virions. In a cytotoxic activity experiment in which the chromium release assay was used to evaluate activity, the results presented in Table 8 were obtained. In these experiments, A3.01 cells are an uninfected control cell line.

TABLE 8

Cytotoxic Activity of NK-92 Cells on HIV-Infected Cells.

| Target | E:T Ratio | % Cytotoxicity |
|---|---|---|
| A3.01 | 50:1 | 43 |
|  | 20:1 | 51 |
|  | 5:1 | 44 |
|  | 1:1 | 44 |
| 8E5L | 50:1 | 43 |
|  | 20:1 | 37 |
|  | 5:1 | 44 |
|  | 1:1 | 40 |
| 8E5 | 50:1 | 76 |
|  | 20:1 | 69 |
|  | 5:1 | 77 |
|  | 1:1 | 65 |

It is seen from Table 8 that 8E5 cells which produce HIV particles elicit a higher cytotoxic activity than do 8E5L cells, which do not produce HIV particles, and higher than control cells. Without wishing to be bound by theory, it is believed that the anti-viral effect of NK-92 cells is due to factors such as a direct cytotoxic effect, as well as inhibition through MIP-1α, which is produced by NK-92 cells in high concentrations (Bluman et al, *J. Clin. Investig.* 97, 2722 (1996)). The results indicate that NK-92 cells effectively lyse HIV-producing cells in vitro.

I claim:

1. A method of treating a cancer in vivo in a mammal comprising the step of administering to the mammal a medium comprising an NK-92 cell line ATCC Deposit No. CRL-2407, wherein said cancer is recognized and lysed by said NK-92 cell line and wherein said cancer is a solid tumor.

* * * * *

UNITED STATES PATENT AND TRADEMARK OFFICE
CERTIFICATE OF CORRECTION

PATENT NO. : 10,138,462 B2
APPLICATION NO. : 10/008955
DATED : November 27, 2018
INVENTOR(S) : Hans Klingemann Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 2874 days.

Signed and Sealed this
Fourth Day of June, 2019

Andrei Iancu
*Director of the United States Patent and Trademark Office*

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:

-continued

```
<223> OTHER INFORMATION: primer oligonucleotide based on human sequence

<400> SEQUENCE: 1
caactcctgt cttgcattgc                                              20

<210> SEQ ID NO 2
<211> LENGTH: 19
<212> TYPE: DNA
<213> ORGANISM: Artificial Sequence
<220> FEATURE:
<223> OTHER INFORMATION: reverse primer oligonucleotide based on human
      sequence

<400> SEQUENCE: 2
gcatcctggt gagtttggg                                               19
```